(12) United States Patent
Kanbara et al.

(10) Patent No.: US 9,518,009 B2
(45) Date of Patent: Dec. 13, 2016

(54) MULTIFUNCTIONAL NITRILEOXIDE COMPOUND

(71) Applicants: DAIKIN INDUSTRIES, LTD., Osaka-shi, Osaka (JP); TOKYO INSTITUTE OF TECHNOLOGY, Tokyo (JP)

(72) Inventors: Tadashi Kanbara, Settsu (JP); Tsuyoshi Noguchi, Settsu (JP); Haruhisa Masuda, Settsu (JP); Haruhiko Mouri, Settsu (JP); Toshikazu Takata, Tokyo (JP); Satoshi Uchida, Tokyo (JP); Yasuhito Koyama, Tokyo (JP); ChenGang Wang, Tokyo (JP); Shunsuke Monjiyama, Tokyo (JP); Hiromitsu Sogawa, Tokyo (JP)

(73) Assignees: DAIKIN INDUSTRIES, LTD., Osaka (JP); TOKYO INSTITUTE OF TECHNOLOGY, Tokyo (JP)

( * ) Notice: Subject to any disclaimer, the term of this patent is extended or adjusted under 35 U.S.C. 154(b) by 0 days.

(21) Appl. No.: 14/640,838

(22) Filed: Mar. 6, 2015

(65) Prior Publication Data

US 2015/0251995 A1    Sep. 10, 2015

(30) Foreign Application Priority Data

Mar. 7, 2014   (JP) .................. 2014-045587
Oct. 21, 2014  (JP) .................. 2014-214923

(51) Int. Cl.
   C07C 291/06    (2006.01)
   C08F 236/14    (2006.01)
   C08F 120/44    (2006.01)

(52) U.S. Cl.
   CPC ................. C07C 291/06 (2013.01)

(58) Field of Classification Search
   CPC .................. C07C 291/06
   USPC ........ 525/329.3, 329.1, 331.9; 560/38; 564/300
   See application file for complete search history.

(56) References Cited

U.S. PATENT DOCUMENTS

2011/0054134 A1   3/2011   Seo et al.
2011/0224380 A1   9/2011   Seo et al.

FOREIGN PATENT DOCUMENTS

| JP | 2010-37288 A | 2/2010 |
| JP | 2010-37289 A | 2/2010 |
| JP | 2011-52072 A | 3/2011 |
| JP | 2011-208117 A | 10/2011 |
| JP | 2013-112741 A | 6/2013 |

OTHER PUBLICATIONS

Wang Chen-Gang et al., Polymer nitrile N-oxides directed toward catalyst- and solvent-free click grafting, Chem. Commun., 2013, 49, 7723-7725, DOI: 10.1039/c3cc42992j.

*Primary Examiner* — Duc Truong
(74) *Attorney, Agent, or Firm* — Sughrue Mion, PLLC

(57) ABSTRACT

The present invention provides a compound of the formula (I):

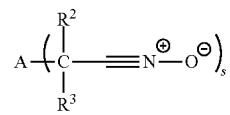

wherein:
   $R^2$ and $R^3$ represent each independently a hydrogen atom or a hydrocarbon group;
   A represents an s-valent organic group; and
   s is an integer of 2-10. This nitrileoxide compound has stable and can be easily produced.

18 Claims, 4 Drawing Sheets

MULTIFUNCTIONAL NITRILEOXIDE COMPOUND

TECHNICAL FIELD

The present invention relates to a multifunctional nitrileoxide compound and a composition comprising the compound.

BACKGROUND ART

A compound having a nitrileoxide group is known to be useful as a reaction agent in various applications since it readily click-reacts with an unsaturated bond in other compound ([2+3] cycloaddition reaction). However, the nitrileoxide compound has problems that a reaction such as dimerization readily occurs and the compound is remarkably unstable. For this problem, it is known that a relative stable nitrileoxide compound can be obtained by modifying it into an aromatic nitrileoxide compound having substituents at ortho positions (Patent Literature 1). Furthermore, with respect to this aromatic nitrileoxide, a multifunctional compound can be synthesized. In addition, a polymer can be cross-linked by using this multifunctional aromatic nitrileoxide (Patent Literatures 2-4).

PRIOR ART LITERATURE

Patent Literature

Patent Literature 1: JP 2011-052072 A
Patent Literature 2: JP 2010-37288 A
Patent Literature 3: JP 2010-37289 A
Patent Literature 4: JP 2011-208117 A
Patent Literature 5: JP 2013-112741 A

Non-Patent Literature

Non-patent Literature 1: Chemical Communications, 2013, p. 7723-7725

SUMMARY OF THE INVENTION

Problem to be Solved by the Invention

However, the aromatic nitrileoxides described in Patent Literatures 1-4 have problems that thermal stability is not sufficient so that the compound quenches (isomerize or dimerize) before raising a reaction of interest in certain applications (for example, applications in which a reaction at high temperature such as a cross-linking (curing) reaction of a fluorine-containing rubber or a reaction in a molding machine is performed).

As a method for solving this problem, a method is known which uses an aliphatic nitrileoxide (a compound having bulky substituents on a carbon atom at the α position of a nitrileoxide group) whose thermal stability is further improved (Patent Literature 5, Non-patent Literature 1). However, since the known aliphatic nitrileoxide is a monofunctional compound, the compound cannot be used in a reaction linking between polymer chains such as a cross-linking (curing) reaction.

Since the known aliphatic nitrileoxide can be produced only by introducing a nitrileoxide group into an alkyl group or one terminal of a carbon chain obtained by polymerizing a polar anion polymerizable monomer or a styrene-based monomer, the structure of the aliphatic nitrileoxide is limited, and the aliphatic nitrileoxide does not meet a requirement for use in any applications.

Furthermore, when based on the known methods, a nitrileoxide group is tried to be introduced into the terminal via an anion polymerization of a ring-opening polymerizable monomer containing a heteroatom such as epoxys, oxetanes, aziridines and cyclic siloxanes or a silicon compounds, a reaction with a nitrostyrene which is a precursor backbone of the nitrileoxide group does not occur, as a result, the nitrileoxide group cannot be introduced into the terminal. It is predicted that the reason for this is that nucleophilicity of an anion species having negative charge on a heteroatom which is produced in a ring-opening polymerization or the like is low. Therefore, it was difficult to introduce a desired backbone containing a heteroatom into the aliphatic nitrileoxide.

Means to Solve the Problem

In the conventional method for synthesizing an aliphatic nitrileoxide, a certain backbone to be introduced is introduced as a carbanion species. When a multifunctional aliphatic nitrileoxide (i.e. a compound having two or more nitrileoxide groups in one molecular) is synthesized according to this method, it is need to generate a nucleophilic molecular having two or more carbanions in one molecular. However, since the carbanion has extremely high nucleophilicity and reactivity, a compound having two or more carbanions in one molecular has lower stability and is likely to decompose in comparison with a compound having only one carbanion. In addition, due to its high reactivity, a reaction of carbanion does not have high selectivity, and some side reaction often occurs. For example, when a difunctional aliphatic nitrileoxide is synthesized, it is need that both two carbanions in one molecular cause a desired reaction, if at least one of two carbanion occurs a side reaction, the molecular cannot be converted to the desired difunctional nitrileoxide of interest.

Therefore, the inventors of the present invention assume that the problem is to introduce a certain backbone to be introduced as a carbanion species in synthesis of the multifunctional aliphatic nitrileoxide having one or more nitrileoxide groups in one molecular.

Therefore, the present invention provides:

[1] A compound of the formula (I):

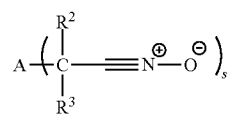

wherein:
$R^2$ and $R^3$ represent each independently a hydrogen atom or a hydrocarbon group;
A represents an s-valent organic group; and
s is an integer of 2-10.

[2] The compound according to the above [1] wherein s is 2 or 3.

[3] The compound according to the above [1] which is represented by the formula (II):

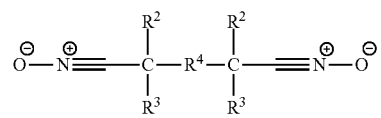

wherein:

R² and R³ represent each independently a hydrogen atom or a hydrocarbon group; and R⁴ represents a di-valent hydrocarbon group;

provided that each of R², R³ and R⁴ binds to a carbon atom to which a nitrileoxide is attached at a carbon atom thereof.

[4] The compound according to any one of the above [1]-[3] wherein R² and R³ are each independently a hydrogen atom, or an alkyl group, a cycloalkyl group, a heterocycloalkyl group, an aryl group, a heteroaryl group or a (poly)alkylether group which may have one or more substituents.

[5] The compound according to any one of the above [1]-[3] wherein at least one of R² and R³ is an aryl group, a tert-alkyl group, a sec-alkyl group or a (poly)alkylether group which may be substituted by one or more substituents.

[6] The compound according to the above [3] wherein R⁴ is a group of the formula:

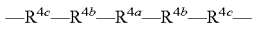

wherein:

$R^{4a}$ represents an alkylene group or a di-valent (poly) alkylether group which may have one or more substituents;

$R^{4b}$ represents each independently a bond, an oxygen atom, or an alkylene group which may have one or more substituents; and $R^{4c}$ represents each independently a bond, or an alkylene group, a cycloalkylene group or an arylene group which may have one or more substituents.

[7] The compound according to the above [6] wherein $R^{4b}$ is —OCO— or —COO—.

[8] The compound according to the above [3] wherein R⁴ is a group of the formula:

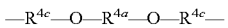

wherein:

$R^{4a}$ represents an alkylene group or a di-valent (poly) alkylether group which may be substituted by one or more substituents; and $R^{4c}$ represents an arylene group.

[9] The compound according to the above [1] which is represented by the formula (III):

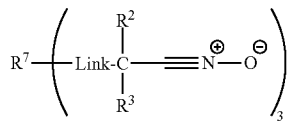

wherein:

R⁷ represents a tri-valent organic group;

R² and R³ represent each independently a hydrogen atom or a hydrocarbon group; and Link represents a bond or a di-valent group;

provided that each of R², R³ and Link binds to carbon atom to which a nitrileoxide is attached at a carbon atom thereof.

[10] The compound according to the above [9] wherein Link represents —$R^{4a}$—, —$R^{4b}$— or —$R^{4c}$—, or a group in which two or more of —$R^{4a}$—, —$R^{4b}$— and —$R^{4c}$— are linked:

wherein $R^{4a}$ represents an alkylene group or a di-valent (poly)alkylether group which may have one or more substituents;

$R^{4b}$ represents each independently a bond, an oxygen atom, or an alkylene group which may have one or more substituents; and $R^{4c}$ represents each independently a bond, or an alkylene group, a cycloalkylene group or an arylene group which may have one or more substituents.

[11] The compound according to the above [9] wherein the Link is an oxygen atom, a sulfur atom, an alkylene group, an alkyleneoxy group, an alkylenedioxy group, a carbonyl group, —O—CO—, —CO—O—, —O—CO—O—, —NR—, —C(O)NR—, —NR—CO—NR— (wherein R is a hydrogen atom or an alkyl group or an aryl group which may have one or more substituents), an arylene group, an aryleneoxy group, an arylenedioxy group, or a group in which two or more of them are linked.

[12] The compound according to any one of the above [9]-[11] wherein R' is preferably C(R) (R is a hydrogen atom or an alkyl group which may be substituted by a fluorine atom), a nitrogen atom, an optionally substituted silicon atom, or a tri-valent aromatic ring which may have a heteroatom as a ring member atom.

[13] A composition comprising one or more compounds according to any one of the above [1]-[12].

[14] A composition comprising for applying to a material containing a group reactive with a nitrileoxide group, which comprises one or more compounds according to any one of the above [1]-[12].

[15] The composition according to the above [13] or [14] which is a cross-linking agent.

[16] The composition according to the above [13] or [14] which is a raw material of for a liquid rubber.

[17] A composite of two or more compounds which are treated with the cross-linking agent according to the above [15].

[18] A liquid rubber produced by using the composition according to the above [16].

Effect of the Invention

According to the present invention, a multifunctional aliphatic nitrileoxide of interest can be obtained by introducing a certain structure of interest into a nitroolefin derivative, and reacting it with carbanion species. In addition, use of the present invention enables synthesis of an aliphatic nitrileoxide compound having a low solubility backbone. Furthermore, by using the method of the present invention, an aliphatic nitrileoxide compound having a backbone containing a heteroatom can be synthesized. In addition, the compound of the present invention can be used as a surface treatment agent, a filler modifier and a reactive compatibilizing agent and provides excellent effects.

EMBODIMENTS TO CARRY OUT THE INVENTION

Figure 1:
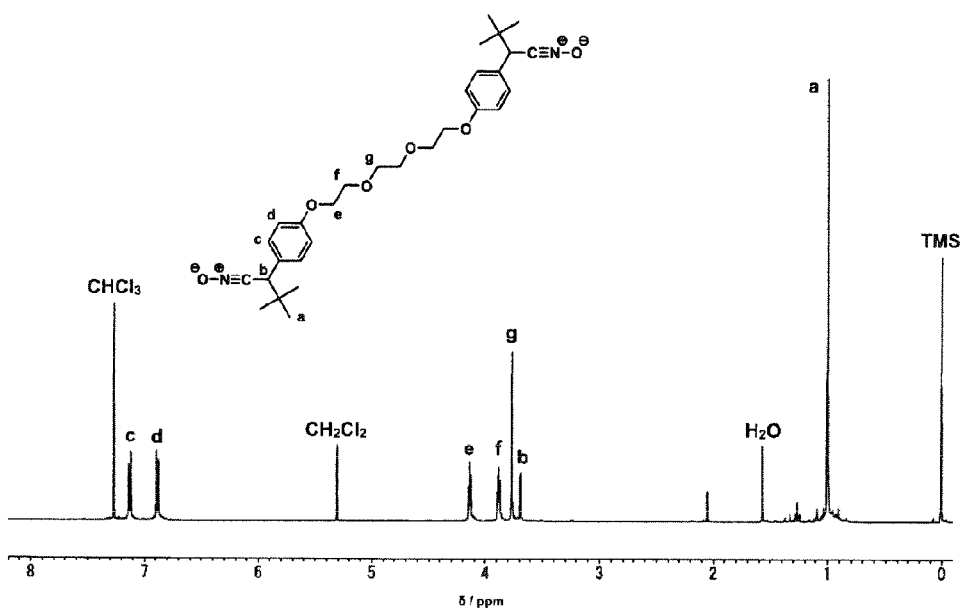
FIG. 1 shows ¹H-NMR spectrum for difunctional t-butyl nitrileoxide 4 in Example 1.

In the present specification, unless otherwise specified, "a hydrocarbon group" means a group containing a carbon atom and a hydrogen atom (provided that, a part of or all of hydrogen atoms may be replaced with the following substituents). Examples of the hydrocarbon group include, but are not particularly limited to, for example, an aliphatic hydrocarbon group, an aromatic hydrocarbon group, and the like, which may be substituted by one or more substituents, a hydrocarbon group having 1-20 carbon atoms. It is noted that the hydrocarbon group may have one or more N, O, S, or the like at its end or in its molecular chain.

In the present specification, unless otherwise specified, the "aliphatic hydrocarbon group" may be straight, branched or cyclic and saturated or unsaturated, and may contain one or more rings. Examples of the "aliphatic hydrocarbon group" include, but are not particularly limited to, an alkyl group, an alkenyl group, an alkynyl group, a cycloalkyl group, a cycloalkenyl group. The "aliphatic hydrocarbon group" may be substituted by one or more substituents.

In the present specification, unless otherwise specified, the "alkyl group" may be straight or branched, and is for example an alkyl group having 1-20, preferably 1-12, more preferably 1-6 carbon atoms. Examples of the "alkyl group" include, but are not particularly limited to, a methyl group, an ethyl group, a propyl group, an isopropyl group, an n-butyl group, an isobutyl group, a sec-butyl group, a tert-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, an n-hexyl group, a 1-methylpentyl group, a 2-methylpentyl group, a 3-methylpentyl group, a 4-methylpentyl group, an n-hexyl group, a 2-methylpentyl group, a 3-methylpentyl group, a 4-methylpentyl group, a 1-ethylbutyl group, a 2-ethylbutyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1,2,2-trimethylpropyl group, a 1-ethyl-1-methylpropyl group, a 1-ethyl-2-methylpropyl group, and the like. The "alkyl group" may be substituted by one or more substituents.

In the present specification, unless otherwise specified, the "alkenyl group" may be straight or branched, and is for example an alkenyl group having 2-20, preferably 2-12, more preferably 2-6 carbon atoms. Examples of the "alkenyl group" include, but are not particularly limited to, for example, a group which at least one carbon-carbon single bond in the above alkyl group is replaced with a carbon-carbon double bond, specifically, a vinyl group, an allyl group, a 1-propenyl group, an isopropenyl group, a 2-methyl-1-propenyl group, a 2-methyl-2-propenyl group, a 1-butenyl group, a 2-butenyl group, a 3-butenyl group, a 1-pentenyl group, a 1-hexenyl group, a 1,3-hexadienyl group, a 1,5-hexadienyl group, and the like. The "alkenyl group" may be substituted by one or more substituents.

In the present specification, unless otherwise specified, the "alkynyl group" may be straight or branched, and is for example an alkynyl group having 2-20, preferably 2-12, more preferably 2-6 carbon atoms. Examples of the "alkynyl group" include, but are not particularly limited to, for example, a group which at least one carbon-carbon single bond in the above alkyl group is replaced with a carbon-carbon triple bond, specifically, an ethynyl group, a 1-propynyl group, a 2-propynyl group, a 1-butynyl group, a 2-butynyl group, a 3-butynyl group, a 1-methyl-2-propynyl group, a 1-pentynyl group, a 1-ethyl-2-propynyl group, a 1-hexynyl group, a 2-hexynyl group, and the like. The "alkynyl group" may be substituted by one or more substituents.

In the present specification, unless otherwise specified, the "cycloalkyl group" is a cyclic alkyl group having 3-20, preferably 5-12 carbon atoms. Examples of the "cycloalkyl group" include, but are not particularly limited to, for example, a cyclopropyl group, a cyclobutyl group, a cyclopentyl group, a cyclohexyl group, a cycloheptyl group, a cyclooctyl group, and the like. The "cycloalkyl group" may be substituted by one or more substituents.

In the present specification, unless otherwise specified, the "cycloalkenyl group" is a cyclic alkenyl group having 3-20, preferably 5-12 carbon atoms. Examples of the "cycloalkenyl group" include, but are not particularly limited to, for example, a cyclopropenyl group, a cyclobutenyl group, a cyclopentenyl group, a cyclohexenyl group, a cycloheptenyl group, a cyclooctenyl group, and the like. The "cycloalkenyl group" may be substituted by one or more substituents.

In the present specification, unless otherwise specified, the "aromatic hydrocarbon group (hereinafter, referred to as an aryl group)" may be monocyclic or polycyclic, for example bicyclic or tricyclic, or may be an aromatic heterocyclic group (hereinafter, referred to as a heteroaryl group). Examples of the "aromatic hydrocarbon group" include, but are not particularly limited to, an aryl group having 3-20 carbon atoms such as a phenyl group, a naphthyl group, and a heteroaryl group having 3-20 carbon atoms such as a furyl group, a thienyl group, a pyridyl group, an indolyl group, a quinolyl group, an isoquinolyl group, or an imidazolyl group. The "aromatic hydrocarbon group" may be substituted by one or more substituents.

In the present specification, unless otherwise specified, the "alkylene group" means a di-valent group which one hydrogen atom on a carbon atom of the above alkyl group is removed.

In the present specification, unless otherwise specified, the "(poly)alkyl ether group" means a group in which an etheric oxygen atom is inserted to one or more carbon-carbon bonds of the above alkyl group.

Preferable (poly)alkyl ether group is a group of the following formula:

wherein R is a $C_{1-16}$ alkyl group, m is an integer of 1-300, and n is an integer of 1-6 at each occurrence.

Preferable (poly)alkyl ether group is a group of the following formula:

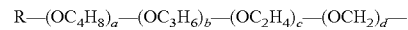

wherein:

R represents a $C_{1-16}$ alkyl group;

a, b, c and d are each independently an integer of 0 or more and 200 or less, the sum of a, b, c and d is one or more, and the occurrence order of the respective repeating units in parentheses with the subscript a, b, c or d is not limited in the formula.

When the (poly)alkyl ether group is used as a di-valent group, it means a group of the following formula:

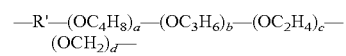

wherein R' represent a $C_{0-16}$ alkylene group. It is noted that in the present specification, $C_0$ means an absence of a carbon atom. For example, a $C_{0-16}$ alkylene group means a bond and a $C_{1-16}$ alkylene group.

In the present specification, unless otherwise specified, examples of the substituents for the hydrocarbon group, the alkyl group, the alkenyl group, the alkynyl group, the cycloalkyl group, the cycloalkenyl group, the aromatic hydrocarbon group and the alkylene group include, but are not particularly limited to, for example, an oxygen atom; a halogen atom; a hydroxyl group; an unsubstituted, mono-substituted or di-substituted amino group; a nitro group; an azide group; a $C_{1-16}$ alkyl group, a $C_{2-16}$ alkenyl group, a $C_{2-16}$ alkynyl group, a $C_{3-16}$ cycloalkyl group, a $C_{3-16}$ cycloalkenyl group, a $C_{6-16}$ heterocycloalkyl group, a $C_{6-16}$ heterocycloalkenyl group, a $C_{6-16}$ aryl group, a $C_{6-16}$ heteroaryl group, a $C_{1-16}$ alkoxy group, a $C_{6-16}$ aryloxy, a $C_{1-16}$ alkylthio or a $C_{1-20}$ (poly)alkyl ether group which may be substituted by one or more halogen atoms; —O—C(O)—$OR^a$, —O—C(O)—$NR^a{}_2$, —C(O)—$R^a$, —C(O)—$OR^a$, —$NR^a$—C(O)—$R^a$, —$NR^a$—C($NR^a$)—$R^a$, —C($NR^a$)—$R^a$ or —C($NR^a$)—$NR^a{}_2$ (wherein $R^a$ represents each independently a hydrogen atom, a $C_{1-16}$ alkyl group, a $C_{2-16}$ alkenyl group, a $C_{2-16}$ alkynyl group, a $C_{3-16}$ cycloalkyl group, a $C_{3-16}$ cycloalkenyl group, a $C_{6-16}$ heterocycloalkyl group, a $C_{6-16}$ heterocycloalkenyl group, a $C_{6-16}$ aryl group or a $C_{6-16}$ heteroaryl group).

The "mono-substituted amino group" represents an amino group substituted by one substituent independently selected from the group consisting of a $C_{1-16}$ alkyl group, a $C_{2-16}$ alkenyl group, a $C_{2-16}$ alkynyl group, a $C_{3-16}$ cycloalkyl group, a $C_{3-16}$ a cycloalkenyl group, a $C_{6-16}$ heterocycloalkyl group, a $C_{6-16}$ heterocycloalkenyl group, a $C_{6-16}$ aryl group and a $C_{6-16}$ heteroaryl group, but is not particularly limited thereto. Examples of the "mono-substituted amino group" include, but are not particularly limited to, methylamine, ethylamino, phenylamino, and the like.

The "di-substituted amino group" represents an amino group substituted by two substituents independently selected from the group consisting of a $C_{1-16}$ alkyl group, a $C_{2-16}$ alkenyl group, a $C_{2-16}$ alkynyl group, a $C_{3-16}$ cycloalkyl group, a $C_{3-16}$ a cycloalkenyl group, a $C_{6-16}$ heterocycloalkyl group, a $C_{6-16}$ heterocycloalkenyl group, a $C_{6-16}$ aryl group and a $C_{6-16}$ heteroaryl group, but are not particularly limited thereto. Examples of the "di-substituted amino group" include, but are not particularly limited to, dimethylamino, diethylamino, diphenylamino, and the like.

Examples of the "$C_{1-16}$ alkoxy group" include, but are not particularly limited to, for example, a methoxy group, an ethoxy group, an n-propoxy group, an isopropoxy group, an n-butoxy group, an isobutoxy group, a sec-butoxy group, a tert-butoxy group, an n-pentyloxy group, an isopentyloxy group, a neopentyloxy group, a tert-pentyloxy group, a 1-ethylpropoxy group, an n-hexyloxy group, an isohexyloxy group, a neohexyloxy group, a 2-ethylbutoxy group, and the like.

Examples of the "$C_{6-16}$ aryloxy" include, but are not particularly limited to, for example, phenoxy, naphthyloxy, and the like.

Examples of the "$C_{1-16}$ alkylthio" include, but are not particularly limited to, for example, methylthio, ethylthio, propylthio, isopropylthio, butylthio, sec-butylthio, tert-butylthio, and the like.

In the present specification, unless otherwise specified, the "halogen (or halogen atom)" means a fluorine atom, a chlorine atom, a bromine atom, an iodine atom, and the like.

In the present specification, unless otherwise specified, the "perfluoroalkyl group" means a group which all hydrogen atoms in the above alkyl group are replaced with a fluorine atom, and is represented by —$C_mF_{2m+1}$ wherein m is an integer, specifically an integer of 1-16, for example an integer of 1-12 or 1-6. The "perfluoroalkyl group" may be straight or branched, preferably straight.

In the present specification, there is a case that a carbon atom to which a nitrileoxide group directly attached in the nitrileoxide compound is referred to as "$C^a$".

Hereinafter, the compound of the present invention will be described below.

The present invention provides a compound of the formula (I) (hereinafter, referred to as a "present compound (I)"):

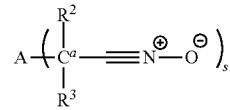

wherein:
$R^2$ and $R^3$ represent each independently a hydrogen atom or a hydrocarbon group;
A represent an s-valent organic group; and
s is an integer of 2-10.

In the formula (I), $R^2$ and $R^3$ represent each independently a hydrogen atom or a hydrocarbon group. Examples of the hydrocarbon group include, but are not particularly limited to, an alkyl group, a cycloalkyl group, a heterocycloalkyl group, an aryl group, or a (poly)alkyl ether group wherein they may have one or more substituents. Preferably, at least one of $R^2$ and $R^3$ is a hydrocarbon group. More preferably, one or both of $R^2$ and $R^3$ are each independently an alkyl group which may be substituted by one or more fluorine atoms or an alkyl group which may be substituted by a (poly)alkyl ether group.

In one embodiment, one or both of $R^2$ and $R^3$ are each independently a fluoroalkyl group or a group (for example, an alkyl group, preferably a sec-alkyl group or a tert-alkyl group, or an aryl group, preferably a phenyl group or an alkyl group) substituted by one or more fluoroalkyl groups. Preferably, the fluoroalkyl group is a fluoroalkyl group wherein a terminal carbon atom is $CF_2H$— and the other carbon atoms are fully substituted by a fluorine atom or a perfluoroalkyl group, more preferably a perfluoroalkyl group. Preferably, one or both of $R^2$ and $R^3$ are each independently an alkyl group substituted a perfluoroalkyl group.

In one embodiment, at least one of $R^2$ and $R^3$ is a phenyl group having an alkoxy group substituted by one or more perfluoroalkyl groups.

In one embodiment, $R^2$ and $R^3$ are preferably a $C_{1-6}$ alkyl group or an aryl group having 3-10 carbon atoms, more preferably, a branched $C_{3-6}$ alkyl group or a phenyl group, particularly preferably a t-Butyl group or a phenyl group.

In the above formula (I), A represent an s-valent organic group, and s is an integer of 2-10, preferably an integer of 2-6, more preferably an integer of 2-4, further preferably 2 or 3, representatively 2.

Examples of A include, but are not limited to, an aliphatic hydrocarbon group or aromatic hydrocarbon group which has divalence, tri-valence or more.

In the above formula (I), each of $R^2$, $R^3$ and A binds to a carbon atom ($C^a$) to which a nitrileoxide is attached at a carbon atom of $R^2$, $R^3$ and A.

In one embodiment, at least one of $R^2$, $R^3$ and A may be substituted by at least one fluorine atom.

In one preferable embodiment, A is a di-valent organic group. A compound of the formula (I) wherein A is a di-valent organic group is represented by the following formula (II):

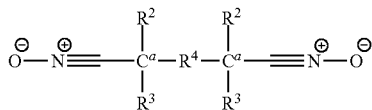

(hereinafter, referred to as a "present compound (II)").

In the above formula (II), $R^2$ and $R^3$ are as defined in the above formula (I).

In the above formula (II), $R^4$ corresponds to A in the formula (I), and represents a di-valent hydrocarbon group.

In one embodiment, $R^4$ is a group $-R^{4a}-$, $-R^{4b}-$ or $-R^{4c}-$, or a group which two or more of them are linked, for example, may be a group of $-R^{4b}-R^{4a}-$, $-R^{4a}-R^{4b}-$, $-R^{4c}-R^{4b}-$, $-R^{4b}-R^{4c}-$, $-R^{4b}-R^{4a}-R^{4b}-$, $-R^{4c}-R^{4b}-R^{4a}-R^{4b}-R^{4c}-$, or the like. Preferably, $R^4$ is a group of the formula: $-R^{4c}-R^{4b}-R^{4a}-R^{4b}-R^{4c}-$.

In the above formula, $R^{4a}$ represents an alkylene group, an arylene group or a di-valent (poly)alkyl ether group which may have one or more substituents, or a group which two or more of them are liked.

In one embodiment, $R^{4a}$ is an alkylene group, an arylene group or a di-valent (poly)alkyl ether group or a di-valent (poly)alkyl ether group.

In another embodiment, $R^{4a}$ is an arylene-alkylene-arylene group.

In one embodiment, the alkylene group may be a straight or branched (preferably straight) $C_{1-10}$ alkylene group, preferably a $C_{2-6}$ alkylene group.

In one embodiment, the arylene group is an arylene group having 3-20 carbon atoms, preferably an arylene group having 3-10 carbon atoms, for example phenylene.

In one embodiment, the di-valent (poly)alkyl ether group is an unsubstituted (poly)alkyl ether, preferably $-(C_{1-6}$ alkylene-O$)_n-$ (n is an integer of 1-10, preferably an integer of 2-6), for example, $-(CH_2CH_2O)_n-$.

In a further embodiment, a substituent for $R^{4a}$ is selected from a halogen atom, preferably a fluorine atom.

In this embodiment, preferably, $R^{4a}$ may be $-C_{0-6}$ alkylene-perfluoroalkylene-$C_{0-6}$ alkylene-, more preferably $-C_{0-6}$ alkylene-perfluoroalkylene-$C_{0-6}$ alkylene-.

The $C_{0-6}$ alkylenes attaching to the both terminals of the perfluoroalkylene may be same or different.

The $C_{0-6}$ alkylene is preferably a straight $-C_{1-6}$ alkylene-, more preferably a straight $-C_{1-3}$ alkylene-, specifically includes methylene, ethylene, or propylene.

The perfluoroalkylene is preferably a straight $C_{1-12}$ perfluoroalkylene, more preferably a straight $C_{3-12}$ perfluoroalkylene, further preferably a straight $C_{3-8}$ perfluoroalkylene.

In this embodiment, more preferably, $R^{4a}$ may be straight $C_{1-3}$ alkylene-straight $C_{3-8}$ perfluoroalkylene-straight $C_{1-3}$ alkylene-.

In the above formula, $R^{4b}$ represents each independently a bond, an oxygen atom, a sulfur atom, a carbonyl group, $-O-CO-$, $-CO-O-$, $-O-CO-O-$, $-NR-$, $-C(O)NR-$, $-NR-CO-NR-$ (wherein R is a hydrogen atom, or an alkyl group or an aryl group which may have one or more substituents), or an alkylene group which may have one or more substituents, preferably an oxygen atom or $-O-CO-$, $-CO-O-$.

In the above formula, $R^{4c}$ represents each independently a bond, or an alkylene group, a cycloalkylene group or an arylene group which may have one or more substituents. Preferably, $R^{4c}$ is an alkylene group or an arylene group whose carbon atom attaching to $C^a$ is secondary or tertiary, preferably a tertiary alkylene group or an arylene group; more preferably an arylene group, further preferably an phenylene group.

$R^4$ is preferably a group of the formula:

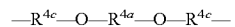

wherein:

$R^{4a}$ represents an alkylene group or a di-valent (poly)alkyl ether group which may have one or more substituents; and $R^{4c}$ represents an arylene group.

In one preferable embodiment, A is an aliphatic hydrocarbon group or an aromatic hydrocarbon group having tri-valence or more.

A compound of the formula (I) wherein A is a tri- or more-valent aliphatic hydrocarbon group is represented by the following formula (III):

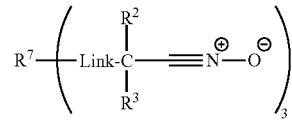

wherein $R^7$ is a tri-valent organic group, and $R^2$ and $R^3$ are as defined in the formula (I).

In the above formula, $R^2$ and $R^3$ are, preferably each independently, an alkyl group or an aryl group which may be substituted by a fluorine atom, more preferably a $C_{1-6}$ alkyl group or an aryl group having 3-10 carbon atoms, further preferably a branched $C_{3-6}$ alkyl group or a phenyl group, particularly preferably a t-Butyl group or a phenyl group.

In the above formula, Link represents a linker. The linker is a bond or a di-valent group, and includes, but is not limited to, for example a di-valent aliphatic hydrocarbon group, a di-valent aromatic hydrocarbon group, and the like.

In one embodiment, Link may be $-R^{4a}-$, $-R^{4b}-$ or $-R^{4c}-$ described for the formula (II), or a group which two or more of them are linked, for example, may be a group of $-R^{4b}-R^{4a}-$, $-R^{4a}-R^{4b}-$, $-R^{4c}-R^{4b}-$, $-R^{4b}-R^{4c}-$, $-R^{4b}-R^{4a}-R^{4b}-$, $-R^{4c}-R^{4b}-R^{4a}-R^{4b}-R^{4c}-$, or the like.

In another embodiment, examples of a preferable linker include, for example, an oxygen atom, a sulfur atom, an alkylene group, an alkyleneoxy group, an alkylenedioxy group, a carbonyl group, $-O-CO-$, $-CO-O-$, $-O-CO-O-$, $-NR-$, $-C(O)NR-$, $-NR-CO-NR-$ (wherein R is a hydrogen atom, or an alkyl group or an aryl group which may have one or more substituents), an arylene group, an aryleneoxy group, an arylenedioxy group, and a group which two or more of them are linked, more preferably an alkyleneoxy group, an alkylenedioxy group, a carbonyloxy-arylene group, an aryleneoxy-arylene group, and the like.

In the formula, $R^7$ is preferably C(R) (R is a hydrogen atom or an alkyl which may be substituted by a fluorine atom), a nitrogen atom, an optionally substituted silicon atom, a tri-valent aromatic ring which may have a heteroatom as a ring member atom, preferably, C(R) (R is a hydrogen atom or an alkyl group) or a tri-valent benzene ring, more preferably $C(CH_3)$ or a benzene ring.

In one embodiment, a compound of the formula (I) wherein A is a tri- or more-valent aliphatic hydrocarbon group is represented for example by the following formula (VI) or the formula (VII):

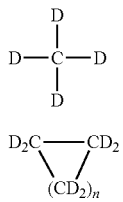
(VI)

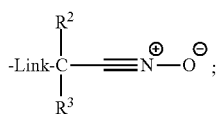
(VII)

wherein:
D represents $R^{20}$ or a group of the formula (a):

$R^{20}$ represents a hydrogen atom or a hydrocarbon group (preferably, a $C_{1-6}$ alkyl group which may be substituted by a fluorine atom);
$R^2$ and $R^3$ are as defined in the formula (I);
Link represents a linker:
or two D present on the same carbon atom or the different carbon atoms represent =O, =$NR^{21}$, =$CR^{21}$, or a $C_{1-10}$ alkylene group, and
$R^{21}$ represents a hydrogen atom or a hydrocarbon group (preferably, a $C_6$ alkyl group):
provided that at least three D are a group of the formula (a).

The linker is a bond or a di-valent group, and includes, but is not limited to, for example, a di-valent aliphatic hydrocarbon group and a di-valent aromatic hydrocarbon group.

In one embodiment, Link may be —$R^{4a}$—, —$R^{4b}$— or —$R^{4c}$— described for the formula (II), or a group which two or more of them are linked, for example, may be a group of —$R^{4b}$—$R^{4a}$—, —$R^{4a}$—$R^{4b}$—, —$R^{4c}$—$R^{4b}$—, —$R^{4b}$—$R^{4c}$—, —$R^{4b}$—$R^{4a}$—$R^{4b}$—, —$R^{4c}$—$R^{4b}$—$R^{4a}$—$R^{4b}$—$R^{4c}$—, or the like.

In another embodiment, examples of a preferable linker include, for example, an oxygen atom, a sulfur atom, an alkylene group, an alkyleneoxy group, an alkylenedioxy group, a carbonyl group, —O—CO—, —CO—O—, —O—CO—O—, —NR—, —C(O)NR—, —NR—CO—NR— (wherein R is a hydrogen atom, or an alkyl group or an aryl group which may have one or more substituents), an arylene group, an aryleneoxy group, an arylenedioxy group, and a group which two or more of them are linked, more preferably an alkyleneoxy group, an alkylenedioxy group, a carbonyloxy-arylene group, an aryleneoxy-arylene group, and the like.

The compound of the formula (I) wherein A is a tri- or more-valent aromatic hydrocarbon group is an aromatic hydrocarbon compound having three or more groups of the formula (a). The aromatic compound may be monocyclic or multicyclic, or carbocyclic or heterocyclic.

For example, examples of the benzene compound of the formula (I) wherein A is a tri or more-valent aromatic hydrocarbon group includes a compound of the following formula (VIII):

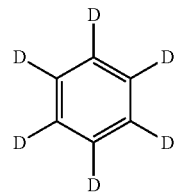

wherein:
D is as defined above:
provided that when D is a group of the formula (a), Link in the formula (a) is not a bond.

In a preferable embodiment, the compound of the formula (VIII) is a compound of the formula (VIIIa) having three nitrileoxide groups:

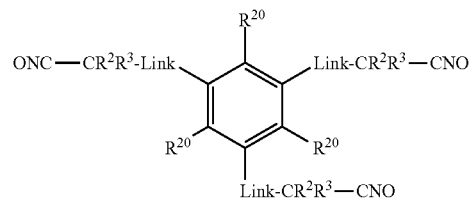

wherein:
$R^2$, $R^3$, $R^{20}$ and Link are as defined above.

In the above formula (VIIIa), $R^2$ and $R^3$ are, preferably, each independently, an alkyl group or an aryl group, more preferably a $C_{1-6}$ alkyl group or an aryl group having 3-10 carbon atoms, further preferably a branched $C_{3-6}$ alkyl group or a phenyl group, particularly preferably a t-Butyl group or a phenyl group.

In the above formula (VIIIa), preferably, Link is each independently a bond, a carbonyl group, —O—CO—, —CO—O—, an alkyleneoxy group, an alkylenedioxy group or a arylene group, or a group which two or more of them are linked. More preferably, Link is a carbonyloxyarylene group, for example, a carbonyloxyphenylene group.

In another embodiment, Link may be —$R^{4a}$—, —$R^{4b}$— or —$R^{4c}$— described for the formula (II), or a group which two or more of them are linked, for example, may be a group of —$R^{4b}$—$R^{4a}$—, —$R^{4a}$—$R^{4b}$—, —$R^{4c}$—$R^{4b}$—, —$R^{4b}$—$R^{4c}$—, —$R^{4b}$—$R^{4a}$—$R^{4b}$—, —$R^{4c}$—$R^{4b}$—$R^{4a}$—$R^{4b}$—$R^{4c}$—, or the like.

It is noted that in the formula (VIIIa), a benzene ring moiety may be another aromatic group.

Since the compound of the present invention has higher stability, in particular higher thermal stability in comparison with the conventional aromatic multifunctional nitrileoxide compound, it can be suitably used in various applications. In addition, since a certain substituent can be introduced by using a process for producing described below, the compound of the present invention can be designed so as to have excellent stability and reactivity in the desired temperature range.

Next, the process for producing the compound of the present invention will be described.

The compound of the present invention can be produced by a method comprising the following steps:
(a) reacting a compound of the formula ($P^1$):

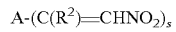

wherein:
R² represents each independently a hydrogen atom or a hydrocarbon group;
A represents an s-valent organic group; and
s is an integer of 2-10, preferably 2 or 3, with a compound of the following formula (Q):

R³L wherein:
R³ represents a hydrogen atom or a hydrocarbon group;
L represents MX$_t$;
M represents Li, Zn, Na, K, Al, Cu, B, Si, Ti, Cr, Fe, Ni, Pd, Pt, Rh, Ru, Ir, Mg or Sm;
X represents a halogen atom or an alkoxy group; and
t represents an integer of 0-6;
and then
(b) dehydrating; and, optionally
(c) converting R², R³ and R⁴ to other R², R³ and R⁴.

For example, a compound having two nitrileoxide groups, that is, a compound of the formula (II) of the present invention can be produced by a method comprising the following steps:
(i) reacting a compound of the formula (P²):

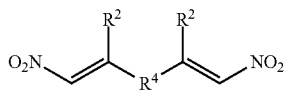

wherein:
R² represents each independently a hydrogen atom or a hydrocarbon group; and
R⁴ represents a di-valent hydrocarbon group;
with a compound of the following formula (Q):

R³L wherein:
R³ represents a hydrogen atom or a hydrocarbon group;
L represents MX$_t$;
M represents Li, Zn, Na, K, Al, Cu, B, Si, Ti, Cr, Fe, Ni, Pd, Pt, Rh, Ru, Ir, Mg or Sm;
X represents a halogen atom or an alkoxy group; and
t represents an integer of 0-6;
and then
(ii) dehydrating; and, optionally
(iii) converting R², R³ and R⁴ to other R², R³ and R⁴.

Firstly, Step (i) will be described.
The compound of the formula (P²) is commercially available or can be produced by a known method.
For example, the compound of the formula (P²) can be obtained by reacting a compound of the following formula (p):

Y—R⁴¹—Y wherein:
Y represents a leaving group, for example a halogen atom, and
R⁴¹ represents a di-valent group which is a part of R⁴;
with 2 equivalents of a compound of the following formula (q):

Z—R⁴²—COR² wherein:
Z represents a nucleophilic group, for example a hydroxyl group,
R⁴² represents a di-valent group which is a part of R⁴, and
R² is as defined above.

In such reaction, Y group in the formula (p) and Z group in the formula (q) are reacted, and R⁴¹, R⁴² and a residue of Z group constitute R⁴ to obtain a compound of C(O)R²—R⁴—C(O)R². Then, this compound of C(O)R²—R⁴—C(O)R² is reacted with CH₃NO₂ to obtain a compound of the formula (P). These reactions can be performed in a suitable solvent and by using a suitable catalyst. Those skilled in the art can select them depending on the compound used.

In the formula (Q), L represents MX$_t$. M represents Zn, Na, K, Al, Cu, B, Si, Ti, Cr, Fe, Ni, Pd, Pt, Rh, Ru, Ir, Mg or Sm, preferably Li, Zn, Na, Cu, B or S particularly preferably, Li or Mg (i.e. an organolithium reagent or Grignard reagent). X represents a halogen atom or an alkoxy group. t represents an integer of 0-6. The compound of the formula (Q) is an agent having strong nucleophilicity, preferably Grignard reagent, alkyllitium. The compound can be produced by a known method from commercially available compound.

A molar ratio of the compound of the formula (P²) to the compound of the formula (Q) is not limited as long as the ratio is 1:2 or more, usually it is 1:2 to 1:5.

The reaction is performed usually in a solvent. The solvent is not limited as long as the nucleophile of the formula (Q) is not quenched, and include, for example, cyclic ethers such as THF, non-cyclic ethers such as diisopropyl ether, chlorine-containing solvents such as dichloromethane and 1,2-dichloroethane, HMPA (hexamethylphosphamide), DMPU (dimethylpropylene), TMEDA (tetramethylethylenediamine), aromatic compounds such as toluene.

A reaction temperature is appropriately selected depending on the nucleophile of the formula (Q) used, for example, is a temperature at which the nucleophile dis not quenched. Those skilled in the art can determine such temperature.

A reaction time is usually 10 minutes to 24 hours, for example 30 minute to 3 hours.

The reaction may be performed in the presence of a catalyst. Examples of the catalyst include, but are not particularly limited to, HMPA (hexamethylphosphoric triamide), DMPU (N,N'-dimethylpropyleneurea), TMEDA (tetramethylethylenediamine), a crown ether, and the like.

Next, Step (ii) will be described.
The dehydration treatment can be performed by using concentrated sulfuric acid, trifluoromethanesulfonic acid, trifluoromethanesulfonimide or phenylisocyanate, or other strong acid having pair anion having no nucleophilicity, but are not particularly limited thereto.

A treatment temperature is usually 0° C. to a room temperature.

A treatment time is usually 1 minute to 60 minutes, for example 10 minutes to 30 minutes.

Next, Step (iii) will be described.
Step (iii) is an optional step in which R², R³ and R⁴ groups in the obtained nitrileoxide compound are converted to other group, and can be performed for example by substituting the group with other group, or by introducing further substituent. Those skilled in the art can appropriately carry out this step by the method known in the art.

For example, the trifunctional nitrileoxide of the formula (III) can be produced for example by a method comprising the following steps:
(i) reacting a compound of the following formula (P³):

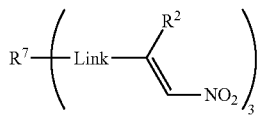

wherein:

R² and Link are as defined in the formula (III); with a compound of the following formula (Q³):

R³L    (5)

wherein:
R³ represents a hydrogen atom or a hydrocarbon group;
L represents MX$_t$;
M represents Li, Zn, Na, K, Al, Cu, B, Ti, Cr, Fe, Ni, Pd, Pt, Rh, Ru, Ir, Mg or Sm;
X represents a halogen atom or an alkoxy group; and
t represents an integer of 0-6;
and then
(ii) dehydrating; and, optionally
(iii) converting R² and R³ to other R² and R³.

Firstly, Step (i) will be described.

The compound of the formula (P³) is commercially available or can be produced by a known method.

For example, the compound of the formula (X4) can be obtained by reacting a compound of the following formula (p'):

R⁶¹(Y)₃ wherein:
Y represents a leaving group, for example a halogen atom, and
R⁶¹ represents a tri-valent group which is a part of R⁷-(Link-)₃
with 3 equivalents of the compound of the following formula (q'):

Z—R⁶²—COR² wherein:
Z represents a nucleophilic group, for example a hydroxyl group,
R⁶² represents a di-valent group which is a part of R⁷-(Link-)₃, and
R² is as defined above.

In the reaction, Y group in the formula (p') and Z group in the formula (q') are reacted, and R⁶¹, R⁶² and a residue of Z group constitute R⁷-(Link-)₃ to obtain the compound of R⁷-(Link-C(O)R²)₃. Then, this compound of R⁷-(Link-C(O)R²)₃ is reacted with CH₃NO₂ to obtain the compound of the formula (P³). These reactions can be performed in a suitable solvent and by using a suitable catalyst. Those skilled in the art can select them depending on compounds used.

In the formula (Q³), L represents MX$_t$. M represents Li, Zn, Na, K, Al, Cu, B, Si, Ti, Cr, Fe, Ni, Pd, Pt, Rh, Ru, Ir, Mg or Sm, preferably Li, Zn, Na, Cu, B or Si, particularly preferably, Li or Mg (i.e. an organolithium reagent or Grignard reagent). X represents a halogen atom or an alkoxy group. t represents an integer of 0-6. The compound of the formula (X) is an agent having strong nucleophilicity, preferably Grignard reagent, alkyllitium. The compound can be produced by known method from commercially available compound.

A molar ratio of the compound of the formula (P³) to the compound of the formula (Q³) is not limited as long as the ratio is 1:3 or more, usually it is 1:3 to 1:8.

The solvent, temperature, reaction time, catalyst, and the like used in the reaction may be the same as those in the above-mentioned synthesis of the di-valent nitrileoxide.

Steps (ii) and (iii) can be performed similarly to the above-mentioned synthesis of the di-valent nitrileoxide.

As a specific embodiment, a synthesis scheme for a compound having three nitrileoxide groups is shown below.

Alternatively, the multifunctional nitrileoxide compound of the present invention can be obtained by synthesizing a monofunctional nitrileoxide having a nucleophilic functional group, and reacting it with a compound having a plurality of a $R^{50}$—CO— group (wherein $R^{50}$ is a leaving group, for example a halogen atom), or a TsO— group (a tosyloxy group), a TfO— group (a triflate group) or X— (a halo group) as a leaving group to obtain the desired multifunctional aliphatic nitrileoxide. It is noted that in the $R^{50}$—CO— group, $R^{50}$ leaves, and the —CO-moiety does not leave.

Examples of the nucleophilic functional group include, but are not limited to, for example, —OH, —SH, —NH$_2$, NHR$^{51}$ (wherein R$^{51}$ is an alkyl group or an aryl group), and the like, preferably —OH.

$R^{50}$ is preferably a halogen atom, specifically a fluorine atom, a chlorine atom, a bromine atom or an iodine atom, R—COO— (wherein an alkyl group or an aryl group, preferably an alkyl group), preferably a chlorine atom.

For example, the multifunctional nitrileoxide compound of the present invention can be obtained by reacting compound of the following formula (D1):

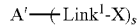

wherein:
A' represents an s-valent organic group,
Link$^1$ represents a di-valent organic group as a linker,
X represents a $R^{50}$—CO— group (wherein $R^{50}$ is a leaving group, for example, a methyl group which may be substituted by a fluorine atom, a halogen atom), or a TsO— group (a tosyloxy group), a TfO— group (a triflate group) or X— (a halo group) as a leaving group, and
s is an integer of 2-10, preferably 2 or 3, with a compound of the following formula (D2):

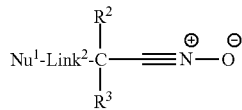

wherein:
R$^2$ and R$^3$ are as defined in the formula (I),
Nu$^1$ is —OH, —SH, —NH$_2$, —NHR$^{51}$ wherein R$^{51}$ is an alkyl group or an aryl group,
Link$^2$ represents a di-valent organic group as a linker.
By the above reaction, a compound of the following formula (D3) can be obtained:

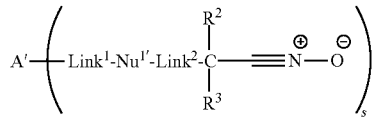

wherein:
A', Link$^1$, Link$^2$, R$^2$ and R$^3$ are as defined above,
s is an integer of 2-10, preferably 2 or 3, and
Nu$^{1'}$ is a group which H is removed from Nu$^1$, can be obtained. That is, in the formula (D3), a moiety from A' to Link$^2$ corresponds to A of the formula (I).

In this reaction, the compound of the formula (D2) is reacted at at least s mole with respect to 1 mole of the compound of the formula (D1).

This reaction is performed in the presence of a base reagent. Examples of the base reagent include, but are not limited to, triethylamine, pyridine, and the like, preferably trimethylamine.

When the difunctional nitrileoxide is synthesized by this reaction, as the compound of the formula (D1), a compound of the following formula (D4) is used:

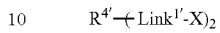

wherein:
R$^{4'}$ is a di-valent organic group,
Link$^{1'}$ is a di-valent organic group, and
X is as defined in the formula (D1).
The compound obtained by the above reaction of the compound of the formula (D4) and the compound of the formula (D2) corresponds to the compound of the formula (II), and -Link$^2$-Nu$^{1'}$-Link$^{1'}$-R$^{4'}$-Link$^{1'}$-Nu$^{1'}$-Link$^2$- corresponds to R$^4$ of the formula (II). For example, Link$^{1'}$ and Link$^2$ may correspond to —R$^{4a}$—, —R$^{4b}$— or —R$^{4c}$— described for the formula (II), or a group which two or more of them are linked.

When a trifunctional nitrileoxide is synthesized by this reaction, as the compound of the formula (D1), a compound of the following formula (D5) is used:
wherein:
R$^7$ is a tri-valent organic group,
Link$^{1'}$ is a di-valent organic group, and
X is as defined in the formula (D1).
The compound obtained by the above reaction of the compound of the formula (D5) and the compound of the formula (D2) corresponds to the compound of the formula (III), and R$^{7'}$-(Link$^{1'}$-Nu$^{1'}$-Link$^2$-)$_3$ corresponds to R$^7$-(Link-)$_3$ of the formula (III). That it, PC corresponds to R$^7$, and -Link$^{1'}$-Nu$^{1'}$-Link$^2$- corresponds to Link-. For example, Link$^{1'}$ and Link$^2$ may correspond to —R$^{4a}$—, —R$^{4b}$— or —R$^{4c}$— described for the formula (II), or a group in which two or more of them are linked.

For example, the following nitrileoxide having OH group as a nucleophilic functional group:

(ONC)(R$^2$)(R$^3$)C—R$^{31}$—OH wherein R$^2$ and R$^3$ are as defined above, and R$^{31}$ is a di-valent organic group;
is reacted with the following compound having a plurality of carbonyl halide:

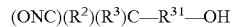

wherein:
A' represents a s'-valent organic group,
s' is an integer of 2-10, and
R$^{50}$ is as defined above
to obtain a multifunctional nitrileoxide of the following formula.

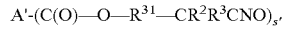

In one embodiment, R$^{31}$ may be —R$^{4a}$—, —R$^{4b}$— or —R$^{4c}$— described for the formula (II), or a group which two or more of them are linked, for example, may be a group of —R$^{4b}$—R$^{4a}$—, —R$^{4a}$—R$^{4b}$—, —R$^{4c}$—R$^{4b}$—, —R$^{4b}$—R$^{4c}$—, —R$^{4b}$—R$^{4a}$—R$^{4b}$—, —R$^{4c}$—R$^{4b}$—R$^{4a}$—R$^{4b}$—R$^{4c}$—, or the like.
R$^{31}$ is preferably an arylene group, more preferably a phenylene group.

As a specific example, a synthesis scheme for a compound having two nitrileoxide groups and a compound having three nitrileoxide groups is shown below.

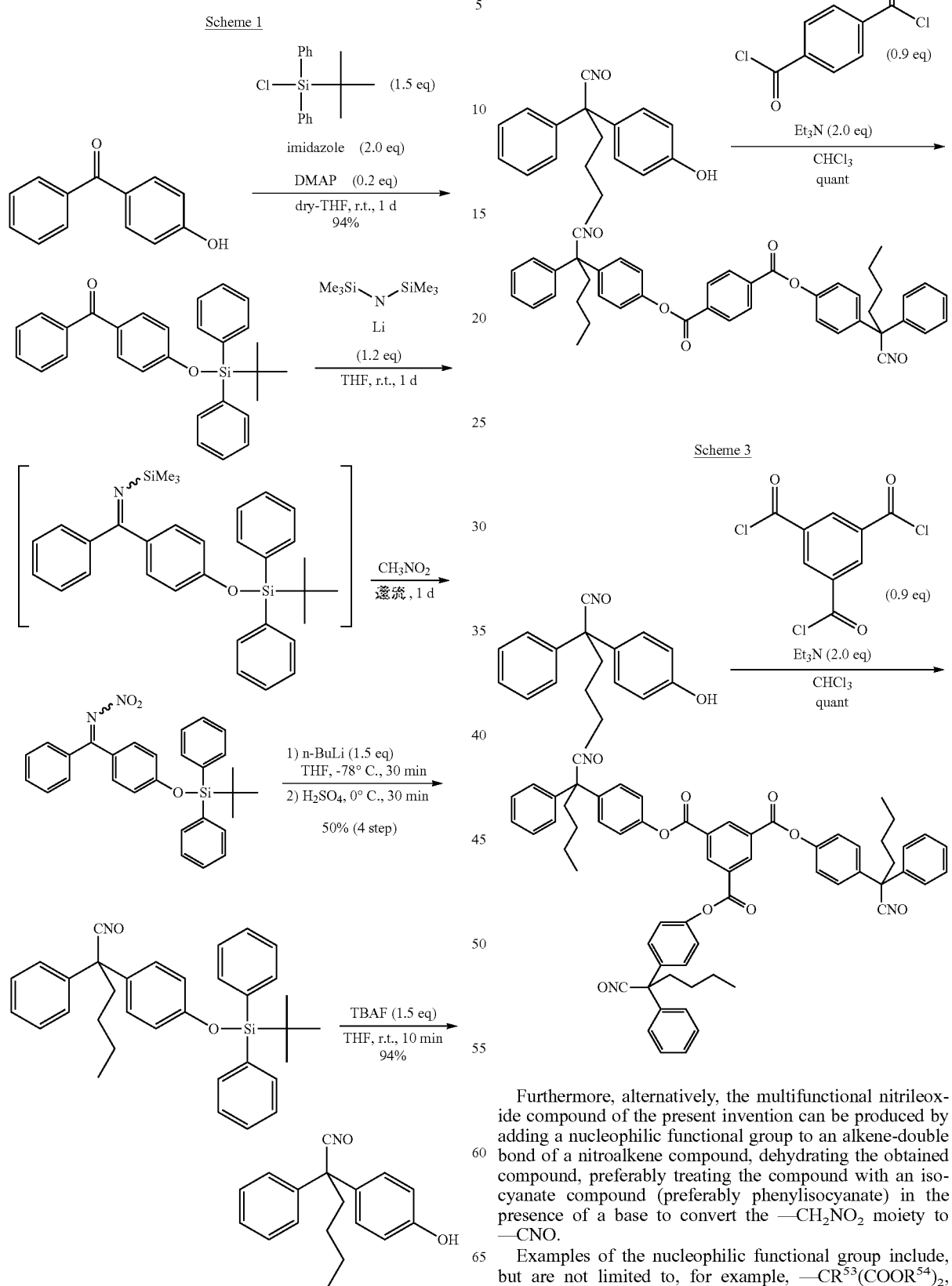

Furthermore, alternatively, the multifunctional nitrileoxide compound of the present invention can be produced by adding a nucleophilic functional group to an alkene-double bond of a nitroalkene compound, dehydrating the obtained compound, preferably treating the compound with an isocyanate compound (preferably phenylisocyanate) in the presence of a base to convert the —CH$_2$NO$_2$ moiety to —CNO.

Examples of the nucleophilic functional group include, but are not limited to, for example, —CR$^{53}$(COOR$^{54}$)$_2$, —OR$^{55}$, —SR$^{55}$, —NR$^{55}$R$^{56}$, and the like, preferably CR$^{53}$ (COOR$^{54}$)$_2$. In the above formula, R$^{53}$ is a fluorine atom, a chlorine atom, or a C$_{1-6}$ alkyl group which may be substituted by one or more fluorine atoms or chlorine atoms, R$^{54}$ is a C$_{1-6}$ alkyl group which may be substituted by one or more fluorine atoms, R$^{55}$ is an alkyl group or an aryl group which may be substituted by a fluorine atom, and R$^{56}$ is a hydrogen atom, an alkyl group or an aryl group.

Preferably, a nitroalkene compound is a compound which a nitroalkene attaches to a benzene ring, preferably a compound which a nitroalkene group attaches to a phenylene-R$^{57}$-phenylene chain. R$^{57}$ is —O—, —S—, —O—CO—, —CO—O—, —O—CO—O—, —NR—, —C(O)NR—, or —NR—CO—NR— wherein R is a hydrogen atom or an alkyl group or an aryl group which may have one or more substituents.

For example, the multifunctional nitrileoxide compound of the present invention can be obtained by reacting the compound of the following formula (E1):

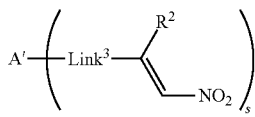

wherein:
A' represents an s-valent organic group,
Link$^3$ represents a di-valent organic group as a linker,
R$^2$ is as defined in the formula (I), and
s is an integer of 2-10, preferably 2 or 3, with a reagent having a nucleophilic functional group:

Nu$^2$H wherein:
Nu$_2$ represents —CR$^{53}$(COOR$^{54}$)$_2$, —OR, —SR$^{55}$ or —NR$^{55}$R$^{56}$, preferably CR$^{53}$(COOR$^{54}$)$_2$,
R$^{53}$ represents a fluorine atom, a chlorine atom, or a C$_{1-6}$ alkyl group which may be substituted by one or more fluorine atoms or chlorine atoms,
R$^{54}$ is a C$_{1-5}$ alkyl group which may be substituted by one or more fluorine atoms,
R$^{55}$ is an alkyl group or an aryl group which may be substituted by a fluorine atom, and
—R$^{56}$ is a hydrogen atom, an alkyl group or an aryl group, to obtain the compound of the formula (E2):

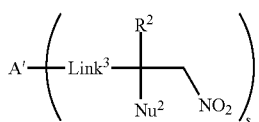

wherein A', Link$^3$, R$^2$ and Nu$^2$ are as defined above,
and then, treating the compound of the formula (E2) with an isocyanate compound, preferably phenylisocyanate to convert the —CH$_2$NO$_2$ moiety to —CNO.

In the compound obtained by this reaction, A'-(Link$^3$-)$_s$ corresponds to A in the compound of the formula (I), and Nu$^2$ corresponds to R$^3$ in the compound of the formula (I). Link$^3$ may correspond to —R$^{4a}$—, —R$^{4b}$—, or —R$^{4c}$— described for the formula (II) or a group which two or more of them are liked When the difunctional nitrileoxide is synthesized by this reaction, as the compound of the formula (E1), a compound of the following formula (E3) is used:

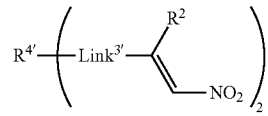

wherein:
R$^{4'}$ is a tri-valent organic group,
Link$^{3'}$ is a di-valent organic group, and
R$^2$ is as defined in the formula (I).

In the compound is obtained by this reaction, R$^{4'}$-(Link$^{3'}$-)$_2$ corresponds to R$^4$ in the formula (II). For example, Link$^{3'}$ corresponds to —R$^{4a}$—, —R$^{4b}$— or —R$^{4c}$— described for the formula (II), or a group which two or more of them are linked.

When the trifunctional nitrileoxide is synthesized by this reaction, as the compound of the formula (E1), the compound of the following formula (E4) is used:

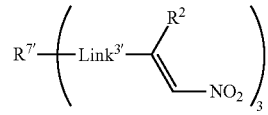

wherein
R$^{7'}$ is a tri-valent organic group,
Link$^{3'}$ is a di-valent organic group, and
R$^2$ is as defined in the formula (I).

In the compound is obtained by this reaction, R$^{7'}$-(Link$^{3'}$-)$_3$ corresponds to R$^7$-(Link-)$_3$ in the formula (III). For example, Link$^{3'}$ corresponds to —R$^{4a}$—, —R$^{4b}$— or —R$^{4c}$— described for the formula (II), or a group which two or more of them are linked.

As a specific example, a synthesis scheme for a compound having three nitrileoxide groups is shown below.

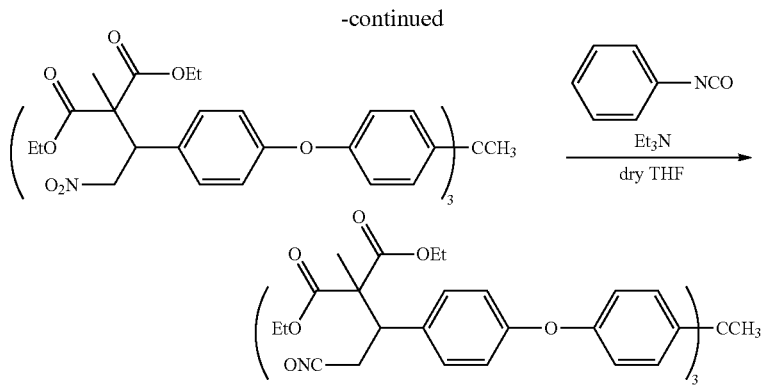

Furthermore, alternatively, the multifunctional nitrileoxide compound of the present invention can be produced by cross-linking two or more nitroalkene compounds with a compound having two or more groups able to add to an alkene-double bond, and then treating the obtained compound with an isocyanate compound, preferably phenylisocyanate in the presence of a base to convert a —CH$_2$NO$_2$ moiety to —CNO.

In this method, preferably, the nitroalkene compound is a compound which a nitroalkene group attaches to a benzene ring.

Examples of the group able to add to an alkene-double bond include, but are not limited to, for example, —OH, —SH, —NH$_2$, —NHR$^{51}$ (wherein, R$^{51}$ is an alkyl group or an aryl group), and the like, preferably —OH.

The compound having a group able to add to an alkene-double bond is preferably a compound wherein the valence-depending number of the groups able to add to an alkene-double bond is attached to A in the formula (I).

For example, the multifunctional nitrileoxide compound of the present invention can be synthesized by reacting a compound of the following formula (F1):

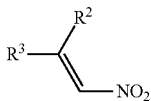

wherein R$^2$ and R$^3$ are as defined in the formula (I), with a compound of the following formula (F2):

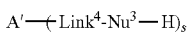

wherein A' represents an s-valent organic group,
Link$^4$ represents a di-valent organic group as a linker,
Nu$^3$ is a nucleophilic functional group, and
s is an integer of 2-10, preferably 2 or 3, to a compound of the following formula (F3):

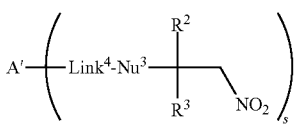

wherein A', Link$^4$, Nu$^3$, R$^2$, R$^3$ and s are as defined above, and then, treating this compound with an isocyanate compound, preferably phenylisocyanate to convert the —CH$_2$NO$_2$ moiety to —CNO.

In the compound obtained by this reaction, A'-(Link$^4$-Nu$^3$-) corresponds to A in the compound of the formula (I). For example, Link$^4$ may correspond to —R$^{4a}$—, —R$^{4b}$— or —R$^{4c}$— described for the formula (II), or a group in which two or more of them are linked.

Nu$^3$ is preferably —O—, —S—, or —NR— (R is an alkyl group or an aryl group).

A' and s are, when the difunctional nitrileoxide is synthesized, R$^{4'}$ (a di-valent organic group) and 2, respectively, and when the trifunctional nitrileoxide is synthesized, R$^{7'}$ (a tri-valent organic group) and 3. In the compound obtained by this reaction, R$^{4'}$-(Link$^4$-Nu$^3$-)$_2$ corresponds to R$^4$ in the formula (II), and R$^{7'}$-(Link$^4$-Nu$^3$-)$_3$ corresponds to R$^7$-(Link-)$_3$ in the formula (III). For example, Link$^4$ may correspond to or —R$^{4a}$—, —R$^{4b}$— or —R$^{4c}$— described for the formula (II), a group which two or more of them are linked.

As a specific example, a synthesis scheme for a compound having two nitrileoxide groups is shown below.

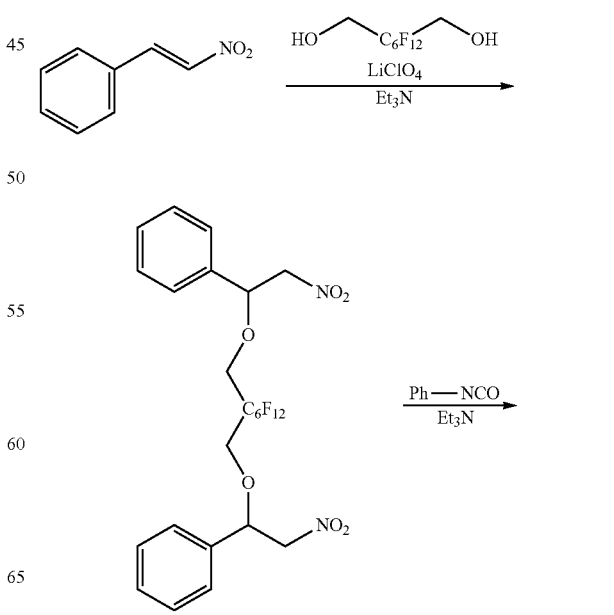

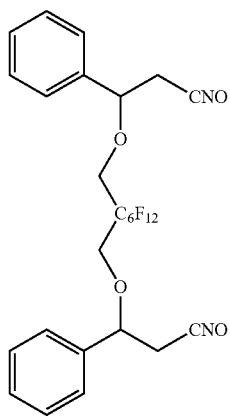

Next, the composition of the present invention will be described.

The present invention provides a composition comprising one or more present compounds (I) described above (hereinafter, referred to as a "composition of the present invention"). The composition may be a liquid or a solid. In addition, the composition may consist of the above-mentioned present compound (I).

In one embodiment, the composition of the present invention may contain a material containing a group reactive with a nitrileoxide group in addition to present compound (I). That is, in this embodiment, the composition of the present invention may be a mixture of present compound (I) and the material containing a group reactive with a nitrileoxide group.

In another embodiment, the composition of the present invention may be in the form of combining with other composition, for example the composition containing the material containing a group reactive with a nitrileoxide group. In this embodiment, the composition of the present invention and other composition may be mixed just before use, and be used in a desired application.

In the above combination form, both the composition of the present invention and other composition may be in the form of a liquid, or one may be in the form of a solid (including a gel), or both may be in the form of a solid (including a gel).

The composition of the present invention may comprise a solvent. The solvent can be appropriately selected depending on components contained in the composition.

In a preferable embodiment, the composition of the present invention or the combination form of the composition of the present invention with other composition is used for applying to the material containing a group reactive with a nitrileoxide group.

Examples of the "group reactive with a nitrileoxide group" include a group having a double bond (C=C, C=N, N=N, C=S, P(V)=C, C=P(III), C=As, C=Se, B=N, P(V)=N, C=O), or a group having a triple bond (C≡C, C≡N, C≡P), specifically an alkenyl group, an alkynyl group, and a nitrile group.

Examples of the "material" in the material containing a group reactive with a nitrileoxide group include, but are nor particularly limited to, for example, a base material applied with the following surface treatment agent (e.g. a glass, a resin, etc.), a compound applied with a compatibilizing agent or a cross-linking agent, in particular a polymer compound (e.g. a natural rubber, a synthetic rubber), a filler applied with a filler modifier, and a compound which is a raw material for a liquid rubber (e.g. a compound having a unsaturated bond).

In one embodiment, the composition of the present invention is a surface treatment agent.

The surface treatment agent of the present invention comprises at least one present compound (I) as a main ingredient or an active ingredient, and can form surface-treating layer having water-repellency, oil-repellency, antifouling property, friction durability, surface slip property, or the like, thus is used as an antifouling coating agent. The "main ingredient" means an ingredient whose contents is more than 50% in the surface treatment agent, and the "active ingredient" means an ingredient which remains on a material to be surface-treated to form a surface-treating layer, thereby exhibiting some function (water-repellency, oil-repellency, antifouling property, surface slip property, friction durability, etc.).

The surface treatment agent of the present invention has an advantageous than a surface treatment agent containing a fluorine-containing silane compound which is suitably applied mainly to a glass material, and a surface treatment agent containing a compound having a curable moiety (for example, double bond) which is suitably applied mainly to a resin material in point that it can be suitably applied to any base material as long as it is reactive with a nitrileoxide group.

The composition of the surface treatment agent of the present invention may be selected depending on a function which is desired in the surface-treating layer.

For example, the surface treatment agent may comprise a fluoropolyether compound which may be also understood as a fluorine-containing oil, preferably a perfluoro(poly)ether compound (hereinafter, referred to as a "fluorine-containing oil") in addition to present compound (I). The fluorine-containing oil contributes to increasing of surface slip property of the surface-treating layer.

The fluorine-containing oil may be contained in the surface-treating agent of the present invention, for example, at 0-300 parts by mass, preferably 50-200 parts by mass with respect to 100 parts by mass of present compound (I) (as the total mass when two or more compounds are used; hereinafter the same shall apply).

Examples of the above-mentioned fluorine-containing oil include, but are not particularly limited to, for example, a compound (a perfluoropolyether compound) of the following general formula (A).

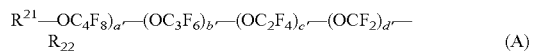

In the formula, $R^{21}$ represents an alkyl group having 1-16 carbon atoms which may be substituted by one or more fluorine atoms, preferably an alkyl group having 1-3 carbon atoms which may be substituted by one or more fluorine atoms. Preferably, the alkyl which may be substituted by one or more fluorine atoms is a fluoroalkyl group in which a terminal carbon atom is $CF_2H$— and the other carbon atoms are fully substituted by a fluorine atom, or a perfluoroalkyl group, more preferably a perfluoroalkyl group.

$R^{22}$ represents a hydrogen atom, a fluorine atom, or an alkyl group having 1-16 carbon atoms which may be substituted by one or more fluorine atoms, preferably an alkyl group having 1-3 carbon atoms which may be substituted by one or more fluorine atoms. Preferably, the alkyl which may be substituted by one or more fluorine atoms is a fluoroalkyl group in which a terminal carbon atom is $CF_2H$— and the other carbon atoms are fully substituted by a fluorine atom, or a perfluoroalkyl group, more preferably a perfluoroalkyl group.

Subscripts a', b', c' and d' represent the repeating number of each of three repeating units of perfluoropolyether which constitute a main backbone of the polymer, and are each independently an integer of 0 or more and 300 or less, and the sum of a', b', c' and d' is at least 1, preferably 1-100. The occurrence order of the respective repeating units in parentheses with the subscript a', b', c' or d' is not limited in the formula. Among these repeating units, the —(OC$_4$F$_8$)— group may be any of —(OCF$_2$CF$_2$CF$_2$CF$_2$)—, —(OCF(CF$_3$)CF$_2$CF$_2$)—, —(OCF$_2$CF(CF$_3$)CF$_2$)—, —(OCF$_2$CF$_2$CF(CF$_3$))—, —(CC(CF$_3$)$_2$CF$_2$)—, —(OCF$_2$C(CF$_3$)$_2$)—, (OCF(CF$_3$)CF(CF$_3$))—, —(OCF(C$_2$F)CF$_2$)— and —(OCF$_2$CF(C$_2$F$_5$))—, preferably —(OCF$_2$CF$_2$CF$_2$CF$_2$)—. The —(OC$_3$F$_6$)— group may be any of —(OCF$_2$CF$_2$CF$_2$)—, —(OCF(CF$_3$)CF$_2$)— and —(OCF$_2$CF(CF$_3$))—, preferably —(OCF$_2$CF$_2$CF$_2$)—. The —(OC$_2$F$_4$)— group may be any of —(OCF$_2$CF$_2$)— and —(OCF(CF$_3$))—, preferably —(OCF$_2$CF$_2$)—.

Examples of the perfluoropolyether compound of the above general formula (A) include a compound of any of the following general formulae (A1) and (A2) (may be one compound or a mixture of two or more compounds).

$$R^{21}-(OCF_2CF_2CF_2)_{b''}-R^{22} \quad (A1)$$

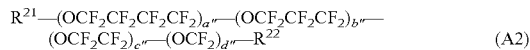

$$R^{21}-(OCF_2CF_2CF_2CF_2)_{a''}-(OCF_2CF_2CF_2)_{b''}-(OCF_2CF_2)_{c''}-(OCF_2)_{d''}-R^{22} \quad (A2)$$

In these formulae:

R$^{21}$ and R$^{22}$ are as defined above; in the formula (A1), b" is an integer of 1 or more and 100 or less; and in the formula (A2), a" and b" are each independently an integer of 1 or more and 30 or less, and c" and d" are each independently an integer of 1 or more and 300 or less. The occurrence order of the respective repeating units in parentheses with the subscript a", b", c" or d" is not limited in the formulae.

The compound of the general formula (A1) and the compound of the general formula (A2) may be used alone or in combination.

When the present compound (I) contains a perfluoroalkyl group, the fluorine-containing oil may be a compound of the general formula Rf$^1$—F wherein R$^1$ is a perfluoroalkyl group contained in present compound (I). In this case, the compound of Rf$^1$—F is preferable because the compound has high affinity for present compound (I).

The surface treatment agent may comprise a silicone compound which may be also understood as a silicone oil (hereinafter referred to as a "silicone oil") in addition to present compound (I). The silicone oil contributes to increasing of surface slip property of the surface-treating layer.

The silicone oil may be contained in the surface treatment agent, for example, at 0-300 parts by mass, preferably 50-200 parts by mass with respect to 100 parts by mass of present compound (I).

Examples of the above-mentioned silicone oil include, for example, a liner or cyclic silicone oil having 2,000 or less siloxane bonds. The liner silicone oil may be so-called a straight silicone oil and a modified silicon oil. Examples of the straight silicone oil include dimethylsilicone oil, methylphenylsilicone oil, and methylhydrogensilicone oil. Examples of the modified silicone oil include that which is obtained by modifying a straight silicone oil with alkyl, aralkyl, polyether, higher fatty acid ester, fluoroalkyl, amino, epoxy, carboxyl, alcohol, or the like. Examples of the cyclic silicone oil include, for example, cyclic dimethylsiloxane oil.

The present invention also provides an article comprising a base material and a layer (a surface-treating layer) which is formed from the above-mentioned present compound (I) or the surface treatment agent (hereinafter, representatively referred to as a "surface-treating composition") on the surface of the base material. This article can be produced, for example, as follows.

Firstly, the base material is provided. As mentioned above, the surface treatment agent of the present invention can be suitably applied to any base material as long as it has reactivity with a nitrileoxide group. The base material usable in the present invention may be composed of any suitable material such as a glass, a resin (may be a natural or synthetic resin such as a common plastic material, and may be in form of a plate, a film, or others), a metal (may be a simple substance of a metal such as aluminum, copper, or iron, or a complex such as alloy or the like), a ceramic, a semiconductor (silicon, germanium, or the like), a fiber (a fabric, a non-woven fabric, or the like), a fur, a leather, a wood, a pottery, a stone, or the like.

For example, when an article to be produced is an optical member, a material constituting the surface of the base material may be a material for an optical member, for example, a glass or a transparent plastic. For example, when an article to be produced is an optical member, any layer (or film) such as a hard coating layer or an antireflection layer may be formed on the surface (outermost layer) of the base material. As the antireflection layer, either a single antireflection layer or a multi antireflection layer may be used. Examples of an inorganic material usable in the antireflection layer include SiO$_2$, SiO, ZrO$_2$, TiO$_2$, TiO, Ti$_2$O$_3$, Ti$_2$O$_5$, Al$_2$O$_3$, Ta$_2$O$_5$, CeO$_2$, MgO, Y$_2$O$_3$, SnO$_2$, MgF$_2$, WO$_3$, and the like. These inorganic materials may be used alone or in combination with two or more (for example, as a mixture). Furthermore, the base material may have an insulating layer, an adhesive layer, a protecting layer, a decorated frame layer (I-CON), an atomizing layer, a hard coating layer, a polarizing film, a phase difference film, a liquid crystal display module, and the like, depending on its specific specification.

The shape of the base material is not particularly limited. The region of the surface of the base material on which the surface-treating layer should be formed may be at least a part of the surface of the base material, and may be appropriately determined depending on use, the specific specification, and the like of the article to be produced.

The base material may be that of which at least the surface consists of a material originally having a group reactive with a nitrileoxide group. On the other hand, by pre-treating the base material, the group reactive with a nitrileoxide group may be introduced to the base material. For example, when the base material is a glass, the group reactive with a nitrileoxide group can be introduced to the base material by treating the base material with a piranha solution to express a hydroxyl group, and reacting this hydroxyl group for example with allyltrichlorosilane.

Next, the film of the above surface-treating agent of the present invention is formed on the surface of the base material, and the film is post-treated, as necessary, and thereby the surface-treating layer is formed from the surface-treating agent.

The formation of the film of the surface-treating agent of the present invention can be performed by applying the above surface-treating agent on the surface of the base material such that the surface-treating agent coats the surface. The method of coating is not particularly limited. For example, a wet coating method or a dry coating method can be used.

Examples of the wet coating method include dip coating, spin coating, flow coating, spray coating, roll coating, gravure coating, micro-gravure coating, bar coating, die coating, and a similar method.

Examples of the dry coating method include vacuum deposition, sputtering, CVD and a similar method. The specific examples of the vacuum deposition include resistance heating, electron beam, high-frequency heating, ion beam, and a similar method. The specific examples of the CVD method include plasma-CVD, optical CVD, thermal CVD and a similar method.

Additionally, coating can be performed by an atmospheric pressure plasma method.

When the wet coating method is used, the surface-treating agent of the present invention is diluted with a solvent, and then it is applied to the surface of the base material. In view of stability of the fluorine-containing compound or the composition and volatile property of the solvent, the following solvents are preferably used: an aliphatic perfluorohydrocarbon having 5-12 carbon atoms (for example, perfluorohexane, perfluoromethylcyclohexane and perfluoro-1, 3-dimethylcyclohexane); an aromatic polyfluorohydrocarbon (for example, bis(trifluoromethyl)benzene); an aliphatic polyfluorohydrocarbon; a hydrofluoroether (HFE) (for example, an alkyl perfluoroalkyl ether such as perfluoropropyl methyl ether ($C_3F_7OCH_3$), perfluorobutyl methyl ether ($C_4F_9OCH_3$), perfluorobutyl ethyl ether ($C_4F_9OC_2H_5$) and perfluorohexyl methyl ether ($C_2F_5CF(OCH_3)C_3F_7$) (the perfluoroalkyl group and the alkyl group may be liner or branched)), and the like. These solvents may be used alone or as a mixture of 2 or more compound. Among them, the hydrofluoroether is preferable, perfluorobutyl methyl ether ($C_4F_9OCH_3$) and/or perfluorobutyl ethyl ether ($C_4F_9OC_2H_5$) are particularly preferable.

After forming the film of the surface treatment agent by using the above method, if necessary, post-treatment may be performed. Examples of the post-treatment include, but are not particularly limited to, for example heating to 40-150° C., for example 60-100° C.

As described above, the surface-treating layer derived from the film of the surface-treating agent of the present invention is formed on the surface of the base material to produce the article of the present invention.

Therefore, the surface treatment agent can be suitably used to form the surface-treating layer on an outermost layer of an optical material. Examples of the optical material include preferably a variety of optical materials: for example, displays such as a cathode ray tube (CRT; for example, TV, personal computer monitor), a liquid crystal display, a plasma display, an organic EL display, an inorganic thin-film EL dot matrix display, a rear projection display, a vacuum fluorescent display (VFD), a field emission display (FED; Field Emission Display), or a protective plate of such displays, or that in which these displays and protective plates have been subjected to antireflection treatment on their surface.

The article having the surface-treating layer obtained according to the present invention is not specifically limited to, but may be an optical member. Examples of the optical member include the followings: lens of glasses, or the like; a front surface protective plate, an antireflection plate, a polarizing plate, or an anti-glare plate on a display such as PDP and LCD; a touch panel sheet of an instrument such as a mobile phone or a personal digital assistance; a disk surface of an optical disk such as a Blu-ray disk, a DVD disk, a CD-R or MO; an optical fiber, and the like.

The thickness of the surface-treating layer is not specifically limited. For the optical member, the thickness of the surface-treating layer is within the range of 0.1-30 µm, preferably 0.5-20 µm, in view of optical performance, friction durability and antifouling property.

The surface-treating layer formed from the surface treatment agent of the present invention may have water-repellency, oil-repellency, antifouling property, surface slip property and/or high friction durability, thus may be suitably used as a functional thin film.

In one embodiment, the composition of the present invention is a filler modifier.

The filler modifier of the present invention comprises at least one present compound (I).

Examples of the filler to which the filler modifier of the present invention is applied include a filler having a group reactive with a nitrileoxide group on its surface, for example, but are not particularly limited to, silica particles, alumina, titanium oxide, barium oxide and calcium oxide in which a group having an unsaturated bond such as a vinyl group, an allyl group, and a nitrile group is introduced on its surface.

The method for introducing the group having an unsaturated bond such as a vinyl group, an allyl group, and a nitrile group to the surface of silica particles is well known by those skilled in the art. For example, introduction of a vinyl group to the surface of the silica particles can be carried out by treating the silica particles with a vinyl-based silane coupling agent (e.g. vinylethoxysilane, or the like).

The modification treatment using the filler modifier can be carried out simply by mixing the filler modifier with the filler. The modification treatment is carried out in a solvent.

Examples of the solvent are not particularly limited as long as it is inert to the compound of the present invention and the filler, and include, for example, water, an aliphatic perfluorohydrocarbon having 5-12 carbon atoms (for example, perfluorohexane, perfluoromethylcyclohexane and perfluoro-1,3-dimethylcyclohexane); an aromatic polyfluorohydrocarbon (for example, bis(trifluoromethyl)benzene); an aliphatic polyfluorohydrocarbon; a hydrofluoroether (HFE) (for example, an alkyl perfluoroalkyl ether such as perfluoropropyl methyl ether ($C_3F_7OCH_3$), perfluorobutyl methyl ether ($C_4F_9OCH_3$), perfluorobutyl ethyl ether ($C_4F_9OC_2H_5$), and perfluorohexyl methyl ether ($C_2F_5CF(OCH_3)C_3F_7$) (the perfluoroalkyl group and the alkyl group may be liner or branched)), and the like.

The present' invention also provides a filler which is treated with the filler modifier, for example silica particles.

The filler which is treated with the filler modifier has effects, for example when it is used as a filler for a fluorine rubber, a perfluoro rubber or a fluororesin, group on the surface of the filler (for example, $SiO_2$ in silica) with a fluorine-containing polymer can be suppressed in comparison with an untreated filler.

In one embodiment, the composition of the present invention is a reactive compatibilizing agent.

The reactive compatibilizing agent of the invention comprises at least one the above mentioned present compound (I), and can improve compatibility between two or more materials (compounds), for example, between a general-purpose polymer reactive with a nitrileoxide group and a fluorine-containing polymer.

The reactive compatibilizing agent of the present invention can be applied to any combination of compounds as long as it is a combination of a compound reactive with a nitrileoxide group and a fluorine-containing compound. In addition, a combination of compounds to be compatibilized (be complexed) may be a combination of three or more compounds, for example, one compound reactive with a nitrileoxide group and two fluorine-containing compounds.

Examples of the compound reactive with a nitrileoxide group include, but are not particularly limited to, a general-purpose polymer having a moiety reactive with a nitrileoxide group (e.g. C=C, C≡N) in its molecular, for example, a natural rubber, NBR (nitrile rubber), EPDM (ethylene-propylene-diene copolymerized rubber), PAN (polyacrylonitrile) and $H_2C=C(R)-(CH_2-CHR)_n-CH_2-CR=CH_2$ (wherein R is each independently a hydrogen atom, a methyl group, an ethyl group or an isobutyl group, and n is an integer of 10-1000).

Examples of the fluorine-containing compound include, but are not particularly limited to, a fluororesin, a fluorine rubber, and the like.

Examples of the fluororesin include a non-melt processable fluororesin, for example, polytetrafluoroethylene (PTFE), and a melt processable fluororesin, and the like.

The PTFE may be a homopolymer of tetrafluoroethylene (TFE), or a modified polytetrafluoroethylene (modified PTFE). In the present specification, "modified PTFE" means a polymer obtained by co-polymerizing TFE with a co-monomer in such a small amount as not to provide melt processability to the resulting copolymer. Examples of the small amount of co-monomer include, but are not limited to, for example, hexafluoropropylene (HFP), chlorotrifluoroethylene (CTFE), trifluoroethylene (TrFE), perfluoro(alkyl vinyl ether) (PAVE), a perfluoro(alkoxyalkyl vinyl ether), a (perfluoroalkyl)ethylene, and the like. The small amount of co-monomer can be used alone or two or more.

Examples of the PAVE include perfluoro(methylvinyl ether), perfluoro(ethylvinyl ether), perfluoro(propylvinyl ether), and the like.

A ratio of the small amount of co-monomer added to the modified PTFE is, when PAVE, a perfluoro(alkoxyalkyl vinyl ether), or the like is used, usually 0.001-1% by mass with respect to the total mass of TFE and the small amount of copolymer, but it is difficult depending on the type.

Examples of the melt processable fluororesin include a tetrafluoroethylene (TFE)/hexafluoropropylene (HEP) copolymer, a TFE/HFP/perfluoro(alkyl vinyl ether) (PAVE) copolymer, a TFE/PAVE copolymer (tetrafluoroethylene-perfluoroalkyl vinyl ether copolymer (PFA) and a tetrafluoroethylene-perfluoro methyl vinyl ether copolymer (MFA)), an ethylene (Et)/TFE copolymer, an Et/TFE/HFP copolymer, polychlorotrifluoroethylene (PCTFE), a chlorotrifluoroethylene (CTFE)/TFE copolymer, an Et/CTFE copolymer, a TFE/vinylidene fluoride (VDF) copolymer, a VDF/HFP/TFE copolymer, a VDF/HFP copolymer, and the like.

Examples of the fluororesin further include a hydroxyl group containing and fluorine containing copolymer containing a fluoroolefin unit and a hydroxyl group-containing radical polymerizable unsaturated monomer unit.

Examples of the fluoroolefin unit include one or more of a tetrafluoroethylene (TFE) unit, a chlorotrifluoroethylene (CTFE) unit, a vinyl fluoride (VF) unit, a vinylidene fluoride (VDF) unit, a hexafluoropropylene (HFP) unit, a trifluoroethylene (TrFE) unit, a perfluoro(alkyl vinyl ether) (PAVE) unit. Examples of the PAVE unit include a perfluoromethyl vinyl ether unit and a perfluoropropylvinyl ether unit.

Examples of the combination of two or more units comprising the TFE unit include a TFE/HFP unit, a TFE/PAVE unit, a TFE/ethylene unit, a TFE/vinyl ether unit, a TFE/vinyl ester unit, a TFE/vinyl ester/vinyl ether unit, a TFE/vinyl ether/allyl ether unit, and the like. Among them, in view of readily mixing with an ethylenically unsaturated group-containing monomer, the TFE/ethylene unit, the TFE/vinyl ether unit, the TFE/vinyl ester unit, the TFE/vinyl ester/vinyl ether unit, the TFE/vinyl ether/allyl ether unit, or the like is preferable.

Examples of the combination of two or more units comprising the CTFE unit include a CTFE/HFP unit, a CTFE/PAVE unit, a CTFE/ethylene unit, a CTFE/vinyl ether unit, a CTFE/vinyl ester unit, a CTFE/vinyl ester/vinyl ether unit, a CTFE/vinyl ether/allyl ether unit, and the like. Among them, in view of readily mixing with an ethylenically unsaturated group-containing monomer, the CTFE/ethylene unit, the CTFE/vinyl ether unit, the CTFE/vinyl ester unit, the CTFE/vinyl ester/vinyl ether unit, the CTFE/vinyl ether/allyl ether unit, or the like is preferable.

Examples of the combination of two or more units comprising the HFP unit include a CTFE/HFP unit, a TFE/HFP unit, a HFP/vinyl ether unit, a HFP/vinyl ester unit, a HFP/vinyl ester/vinyl ether unit, a HFP/vinyl ether/allyl ether unit, and the like. Among them, in view of readily mixing with an ethylenically unsaturated group-containing monomer, the HFP/vinyl ether unit, the HFP/vinyl ester unit, the HFP/vinyl ester/vinyl ether unit, the HFP/vinyl ether/allyl ether unit, or the like is preferable.

Examples of the combination of two or more units comprising the VDF unit include a VDF/TFE unit, a VDF/HFP unit, a VDF/TFE/HFP unit, a VDF/CTFE unit, a VDF/TFE/PAVE unit, a VDF/CTFE/TFE unit, a VDF/CTFE/HFP unit, and the like. Among them, in view of readily mixing with an ethylenically unsaturated group-containing monomer, it is preferable that the VDF unit is contained in the polymer at 50 mol % or more.

Specific examples of the hydroxyl group-containing radical polymerizable unsaturated monomer unit of the hydroxyl group containing and fluorine containing copolymer include, for example, a hydroxyalkyl vinyl ether or a hydroxyalkyl allyl ether of the formula:

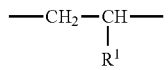

wherein $R^1$ is $-OR^2$ or $-CH_2OR^2$ (wherein $R^2$ is an alkyl group having a hydroxyl group). $R^2$ is, for example, a group which 1-3 hydroxyl groups, preferably one hydroxyl group is linked to a straight or branched alkyl group having 1-8 carbon atoms. Examples of them include, for example, a 2-hydroxyethylvinyl ether unit, a 3-hydroxypropylvinyl ether unit, a 2-hydroxypropylvinyl ether unit, a 2-hydroxy-2-methylpropylvinyl ether unit, a 4-hydroxybutylvinyl ether unit, a 4-hydroxy-2-methylbutylvinyl ether unit, a 5-hydroxypentylvinyl ether unit, 6-hydroxyhexylvinyl ether unit, a 2-hydroxyethylallyl ether unit, a 4-hydroxybutylallyl ether unit, an ethylene glycol monoallyl ether unit, a diethylene glycol monoallyl ether unit, a triethylene glycol monoallyl ether unit, a glycerin monoallyl ether unit, and the like. Among them, a hydroxyalkyl vinyl ether having 1-3 carbon atoms is particularly preferable, and a 4-hydroxybutylvinyl ether unit or a 2-hydroxyethylvinyl ether unit is more preferable in view of easy polymerization.

The hydroxyl group containing and fluorine containing copolymer may further comprise a hydroxyl-free and fluorine-free vinyl ether unit and/or a fluorine-free vinyl ester unit Specific examples of the hydroxyl group-free and fluorine-free vinyl ether unit and/or the fluorine-free vinyl ester unit in the hydroxyl group containing and fluorine containing copolymer include, for example, an alkyl vinyl ether or an alkyl allyl ether of the formula:

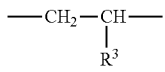

wherein $R^3$ is —$OR^4$, —$COOR^4$ or —$OCOR^4$ (wherein $R^4$ is an alkyl group). $R^4$ is, for example, a straight, branched or cyclic alkyl group having 1-8 carbon atoms. As examples of them, for example, a cyclohexylvinyl ether unit, a methylvinyl ether unit, an ethylvinyl ether unit, a propylvinyl ether unit, an n-butylvinyl ether unit, an isobutylvinyl ether unit, a vinyl acetate unit, a vinyl propionate unit, a vinyl butyrate unit, a vinyl isobutyrate unit, a vinyl pivalate unit, a vinyl caproate unit, a vinyl versatate unit, a vinyl laurate unit, a vinyl stearate unit or a vinyl cyclohexyl carboxylate unit is preferable. Furthermore, in view of excellent weather resistance, solubility and low-cost, vinyl versatate, vinyl laurate, vinyl stearate, a vinyl cyclohexyl carboxylate, or vinyl acetate is preferable. Among them, in view of chemical resistance, a non-aromatic vinyl carboxylate ester, in particular a carboxylic acid vinyl ester having 6 or more carbon atoms in carboxylic acid is preferable, and a carboxylic acid vinyl ester having 9 or more carbon atoms carboxylic acid is more preferable. The upper limit of carbon atoms of carboxylic acid in the carboxylic acid vinyl ester is preferably 20 or less, more preferably 15 or more. As a specific example, vinyl versatate is most preferably.

The hydroxyl group containing and fluorine containing copolymer may contain a carboxyl group-containing monomer unit.

The carboxyl group-containing monomer unit contains a carboxyl group and does not contain a hydroxyl group and an aromatic group, and in this point, it differs from the other units.

Examples of the carboxyl group-containing monomer unit include, for example, a carboxyl group-containing vinyl monomer of the formula:

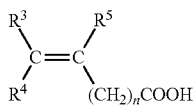

wherein $R^3$, $R^4$ and $R^5$ is same or different, and are a hydrogen atom, an alkyl group, a carboxyl group or an ester group, and n is 0 or 1
or the formula:

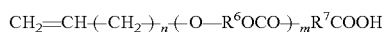

wherein and $R^7$ are same or different, and are a saturated or unsaturated straight or cyclic alkyl group, n is 0 or 1, and m is 0 or 1.

Specific examples of the carboxyl group-containing monomer unit include, for example, one or more selected from acrylic acid, methacrylic acid, vinyl acetate, crotonic acid, cinnamic acid, 3-allyloxy propionic acid, itaconic acid, itaconic acid monoester, maleic acid, maleic acid monoester, maleic anhydride, fumaric acid, fumaric acid monoester, vinyl phthalate and vinyl pyromellitate. Among them, crotonic acid, itaconic acid, maleic acid, maleic acid monoester, fumaric acid, fumaric acid monoester, and 3-allyloxy propionic acid which have low homopolymerizality are preferable.

The lower limit of the ratio of carboxyl group-containing monomer unit is 0.1 mol %, preferably 0.4 mol %, and the upper limit is 2.0 mol %, preferably 1.5 mol %.

Specific examples of the hydroxyl group containing and fluorine containing copolymer include, for example, following compounds:

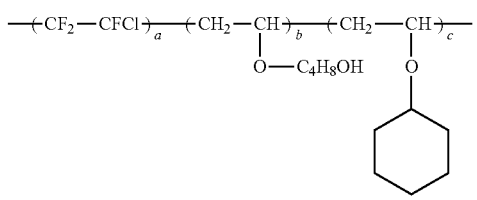

(wherein the formula, the ratio by mole of a, b, and c is a:b:c=40 to 60:3 to 15:5 to 45);

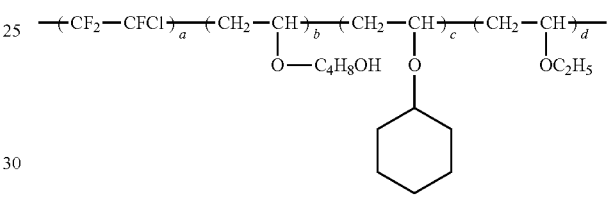

(wherein the formula, the ratio by mole of a, b, and c is a:b:c=40 to 60:3 to 15:5 to 45:5 to 45);

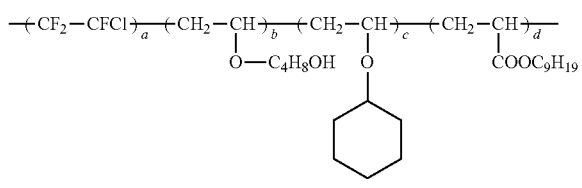

(wherein the formula, the ratio by mole of a, b, c and d is a:b:c:d=40 to 60:3 to 15:5 to 45:5 to 45);

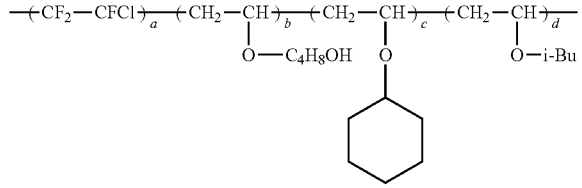

(wherein the formula, the ratio by mole of a, b, c and d is a:b:c:d=40 to 60:3 to 15:5 to 45:5 to 45, and i-Bu represents an isobutyl group); tetrafluoroethylene/vinyl versatate/hydroxybutyl vinyl ether; tetrafluoroethylene/vinyl versatate/hydroxyethyl vinyl ether/tert-butyl vinyl benzoate; tetrafluoroethylene/vinyl versatate/hydroxybutyl vinyl ether/crotonic acid; and tetrafluoroethylene/vinyl versatate/hydroxyethyl vinyl ether/vinyl benzoate/crotonic acid.

Examples of the fluorine rubber include a non-perfluoro fluorine rubber and a perfluoro fluorine rubber.

Examples of the non-perfluoro fluorine rubber include a vinylidene fluoride (VDF) fluorine rubber, tetrafluoroethylene (TFE)/propylene (Pr) fluorine rubber, tetrafluoroethylene (TFE)/propylene/vinylidene fluoride (VDF) fluorine rubber, ethylene/hexafluoropropylene (HFP) fluorine rubber, ethylene/hexafluoropropylene (HFP)/vinylidene fluoride (VdF) fluorine rubber, ethylene/hexafluoropropylene (HFP)/tetrafluoroethylene (TFE) fluorine rubber, fluorosilicone fluorine rubber and fluorophosphazene fluorine rubber. They can be used alone or can be used in arbitrary combinations, as long as the effects of the present invention are not lost. Among them, a vinylidene fluoride fluorine rubber and a tetrafluoroethylene/propylene fluorine rubber are preferable.

The vinylidene fluoride fluorine rubber means a fluorine-containing elastomeric copolymer comprising 45 to 85 mol % of vinylidene fluoride and 55 to 15 mol % of at least one other monomer copolymerizable with vinylidene fluoride. It is preferably referred to fluorine-containing copolymer comprising 50 to 80 mol % of vinylidene fluoride and 50 to 20 mol % of at least one monomer copolymerizable with vinylidene fluoride.

Examples of the at least one other monomer copolymerizable with vinylidene fluoride include, for example, fluorine-containing monomers such as tetrafluoroethylene (TFE), chlorotrifluoroethylene (CTFE), trifluoroethylene, hexafluoropropylene (HFP), trifluoropropylene, tetrafluoropropylene, pentafluoropropylene, trifluorobutene, tetrafluoroisobutene, perfluoro(alkyl vinyl ether) (PAVE), vinyl fluoride, and the like, and fluorine-free monomers such as ethylene, propylene, and alkyl vinyl ether. They can be used alone or in arbitrarily combinations. Among them, tetrafluoroethylene, hexafluoropropylene, and perfluoro (alkyl vinyl ether) are preferable.

In this case, examples of the perfluoro(alkyl vinyl ether) include, for example, perfluoro(methylvinyl ether), perfluoro(propylvinyl ether), and the like. They can be used alone or in arbitrary combinations, as long as the effects of the present invention are not lost.

Examples of the vinylidene fluoride fluorine rubber include a VDF-HFP rubber, a VDF-HFP-TFE rubber, a VDF-CTFE rubber, a VDF-CTFE-TFE rubber, and the like.

The tetrafluoroethylene/propylene fluorine rubber means a fluorine-containing elastomer copolymer comprising 45 to 70 mol % of tetrafluoroethylene, 55 to 30 mol % of propylene, and 0 to 5 mol % of a monomer providing a cross-linking site.

Examples of the monomer providing a cross-linking site include, for example, iodine-containing monomers such as perfluoro(6,6-dihydro-6-iodo-3-oxa-1-hexene) and perfluoro(5-iodo-3-oxa-1-pentene) described in JP 05-63482 B and JP 07-316234 A, bromine-containing monomers described in JP 04-505341 A, cyano group-containing monomers, carboxyl group-containing monomers and alkoxycarbonyl group-containing monomers described in JP 04-505345 A and JP 05-500070 A.

Examples of the perfluoro fluorine rubber include a perfluoro rubber containing TEE, for example, a fluorine-containing elastomer copolymer consisting of TFE/perfluoro(alkyl vinyl ether) (PAVE)/a monomer providing a cross-linking site. The composition is preferably 45 to 90/10 to 50/0 to 5 (mol %), more preferably, 45 to 80/20 to 50/0 to 5, further preferably, 53 to 70/30 to 45/0 to 2. If the composition is out of this range, property as a rubber elastomer is tend to be lost and become property close to a resin property.

In this case, examples of the PAVE include, for example, perfluoro(methylvinyl ether) (PMVE), perfluoro(propylvinyl ether) (PPVE), and the like. They can be used alone or in arbitrary combinations, as long as the effects of the present invention are not lost.

Examples of the monomer providing a cross-linking site include, for example, an iodine-containing monomer of the following formula:

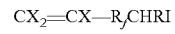
$$CX_2=CX-R_fCHRI$$

wherein X is H, F or $CH_3$, $R_f$ is a fluoroalkylene group, a perfluoroalkylene group, a fluoropolyoxyalkylene group or a perfluoropolyoxyalkylene group, and R is H or $CH_3$,
and a monomer of the following formula:

$$CF_2=CFO(CF_2CF(CF_3))_m-O-(CF_2)_n-Y$$

wherein m is an integer of 0-5, n is an integer of 1-3, Y is a nitrile group, a carboxyl group, an alkoxycarbonyl group or a bromine atom). They can be used alone or in arbitrary combinations, as long as the effects of the present invention are not lost. The iodine atom, the nitrile group, the carboxyl group, the alkoxycarbonyl group, and the bromine atom function as the cross-linking site.

Specific examples of the perfluoro fluorine rubber include a fluorine rubber and the like described in WO 97/24381, JP 61-57324 B, JP 04-81608 B, and JP 05-13961 B.

Examples of the other fluorine-containing polymer include homopolymer such as PVDF (polyvinylidene fluoride), PVF (polyvinyl fluoride).

The reactive compatibilizing agent of the present invention can exert its function simply by mixing the reactive compatibilizing agent containing the compound of the present invention with the compound reactive with a nitrileoxide group and the fluorine containing compound in a step of mixing the compound reactive with a nitrileoxide group and the fluorine containing compound under an atmosphere pressure in a mixing equipment (a kneader, a brabender, an extruder, etc.). In this mixing step, the compound of the present invention click-reacts with a reactive site of the compound reactive with a nitrileoxide group, thereby a fluorine-containing group can be introduced to the compound reactive with a nitrileoxide group. This introduced fluorine-containing group has an affinity for the fluorine-containing compound, thereby enabling compatibilization (complexation) of the both compounds.

The above mixing step is usually carried out at a temperature at which the compound reactive with a nitrileoxide group and the fluorine-containing compound melts, for example, about 150-250° C. For example, when NBR as the compound reactive with a nitrileoxide group is used, and PVDF as the fluorine-containing compound is used, the step is carried out at about 170° C. or more, for example, about 180-210° C. Since the compound of the present invention has a high thermal stability, such treatment at the high temperature can be carried out.

The above mixing step can be carried out usually without a solvent, additives, etc. However, the solvent or additives may be added depending on a purpose, for example in order to accelerate the reaction. Those skilled in the art can select the solvent and the additives depending on a purpose.

Examples of a conventional general compatibilizing agent are a block polymer and a graft polymer which have both backbones of two components to be complexed. The compound of the present invention is advantageous in that the preparation is easy in comparison with the conventional polymer. In addition, the reactive compatibilizing agent of the present invention has an advantage in that it can compatibilize components to be compatibilized simply by mixing the reactive compatibilizing agent with the mixture of the components.

In addition, the present invention provides a composite of two or more compounds treated with the reactive compatibilizing agent of the present invention.

In one embodiment, the composition of the present invention is a fiber treatment agent.

The fiber treatment agent of the present invention contains at least one present compound (I), and can improve water-repellency and oil-repellency of a fiber having a group reactive with a nitrileoxide group, for example, an acrylate fiber.

The fiber treatment agent of the present invention can be suitably used for any fiber as long as it has the group reactive with a nitrileoxide group.

Examples of the fiber include an acrylate fiber, or a polyester fiber or a polyvinyl alcohol fiber obtained by copolymerizing a monomer having a nitrile group in its side chain. In addition, even a fiber having no group reactive with a nitrileoxide group become to be able to be treated with the fiber treatment agent of the present invention by introducing the group reactive with a nitrileoxide group thereto. For example, a polyester fiber or a polyvinyl alcohol fiber obtained by copolymerizing a monomer having a hydroxyl group or an amino group in its side chain become to be able to be treated with the fiber treatment agent of the present invention by dehydration-condensation with a carbonic acid or sulfonic acid compound reactive with a nitrileoxide group.

The fiber treatment agent of the present invention may contain, additives, for example, an emulsifying agent (polyethylene glycol-based, cationic, ammonium, nonionic, anionic), an antifoaming agent, a wetting agent, a paraffin hydrocarbon, and the like in addition to present compound (I).

The fiber treatment agent of the present invention may be diluted with a solvent before being applied to the fiber. Examples of the solvent include, for example, an aliphatic perfluorohydrocarbon having 5-12 carbon atoms (for example, perfluorohexane, perfluoromethylcyclohexane and perfluoro-1,3-dimethylcyclohexane); an aromatic polyfluorohydrocarbon (for example, bis(trifluoromethyl)benzene); an aliphatic polyfluorohydrocarbon; a hydrofluoroether (HFE) (for example, an alkyl perfluoroalkyl ether such as perfluoropropyl methyl ether ($C_3F_7OCH_3$), perfluorobutyl methyl ether ($C_4F_9OCH_3$), perfluorobutyl ethyl ether ($C_4F_9OC_2H_5$)—, and perfluorohexyl methyl ether ($C_2F_5CF(OCH_3)C_3F_7$) (the perfluoroalkyl group and the alkyl group may be liner or branched)), other fluorine solvents, hydrocarbon solvents such as a mineral oil, alcohol, MIBK (methyl isobutyl ketone), glycol-based solvents (ethylene glycol, propylene glycol etc.), and the like.

A method for applying the fiber treatment agent of the present invention to the fiber is not particularly limited as long as it can attach the desired amount of the agent of the fiber to be treated, and various methods can be used. the fiber treatment method includes, be a continuous method or a batch method.

As the continuous method, first, the fiber treatment agent is diluted with a solvent to prepare a treating liquid. Then, an object to be treated is continuously supplied to an impregnation apparatus filled with the treating liquid to impregnate the object to be treated with the treating liquid, and then unnecessary treating liquid is removed. The impregnation apparatus is not particularly limited, and is preferably a padder impregnation apparatus, a kiss roller impregnation apparatus, a gravure coater impregnation apparatus, a spray impregnation apparatus, a foam impregnation apparatus, a coating impregnation apparatus or the like, particularly preferably a padder impregnation apparatus. Then, an operation of removing the solvent remaining in the object is carried out by using a dryer. The dryer is not particularly limited, and is preferably an expansion dryer such as a tenter or a hot flue. This continuous method is employed preferably in a case where the object to be treated is cloth such as woven cloth.

The batch method comprises a step of immersing the object to be treated with a treating liquid, and a step of removing the solvent remaining in the treated object. The batch method is employed preferably in a case where the object to be treated is not cloth, such as a case where it is bulk fiber, top, sliver, hank, tow or thread, or in a case where it is not suitable for the continuous method such as a case where it is knitted fabric. In the immersion step, it is preferred to use, for example, a cotton dyeing machine, a cheese dyeing machine, a jet dyeing machine, an industrial washing machine or a beam dyeing machine. In operation of removing the solvent, it is preferred to use a hot air dryer such as a cheese dryer, a beam dryer or a tumble dryer, or a microwave dryer The treated object to which the fiber treatment agent of the present invention is attached is preferably subjected to a dry heat treatment. When the dry heat treatment is carried cut, active ingredients in the fiber treatment agent of the present invention will more firmly attach to the object to be treated. The temperature for the dry heat treatment is preferably from 120 to 180° C., more preferably from 160 to 180° C. The dry heat treatment time is preferably from 10 seconds to 3 minutes, more preferably from 1 to 2 minutes. The method of the dry heat treatment is not particularly limited, and it is preferred to use a tenter in a case where the object to be treated is cloth.

In addition, the present invention provides a fiber treated with the fiber treatment agent.

The fiber treated with the fiber treatment agent of the present invention has improved water and oil repellency, weather resistance and/or thermal resistance, or the like depending on the compound of the present invention used. In addition, since the compound of the present invention is chemically bonded to the fiber by click-reaction, the above functions are less likely to deteriorate by friction, etc., and can maintain the function for a long time.

In one embodiment, the composition of the present invention is a cross-linking agent.

The cross-linking agent of the present invention contains at least one present compound (I), and can react with two functional groups reactive with a nitrileoxide group and cross-link between these functional groups. It is noted that the two functional groups may be present in same molecular or in different molecular, respectively.

Since nitrileoxide compound (I) of the present invention has higher thermal resistance in comparison with the conventional aromatic multifunctional nitrileoxide, it can be used under a high temperature condition. Therefore, even when a compound to be cross-linked is a polymer having a small amount of reaction sites (that is, unsaturated sites) or a polymer whose back bone is rigid and has poor molecular mobility, these compounds can be cross-linked by subjecting these compounds a treatment under the high temperature condition. Specifically, even a polymer containing tetrafluoroethylene such as a base polymer of the fluorine rubber, a base polymer of the perfluoro rubber, or the like as a main ingredient can be suitably cross-linked.

The compound to be cross-linked is not particularly limited as long as it has a moiety reactive with a nitrileoxide group, and may be, for example, a polymer having a moiety reactive with a nitrileoxide group, for example, a general-purpose rubber, a natural rubber, and a fluoropolymer (preferably a fluorine rubber).

Examples of the general-purpose rubber include, for example, NBR (nitrile rubber), EPDM (ethylene-propylene-diene copolymer rubber), PAN (polyacrylonitrile), $H_2C=C(R)-(CH_2-CHR)_n-CH_2-CR=CH_2$ (wherein R is each independently a hydrogen atom, a methyl group, an ethyl group, or an isobutyl group, and n is an integer of 10-1000).

The natural rubber is a rubbery polymer, and usually has a polyisoprene structure, although is not limited thereto.

The fluorine rubber may be either a non-perfluoro fluorine rubber or a perfluoro fluorine rubber, for example, and preferably has a structural unit derived from at least one monomer selected from the group consisting of tetrafluoroethylene (TFE), vinylidene fluoride (VdF) and a perfluoroethylenically unsaturated compound (for example, hexafluoropropylene (HFP), perfluoro(alkyl vinyl ether)(PAVE), and the like) of the following formula (a):

$$CF_2=CF-Rf^a \quad (a)$$

wherein $Rf^a$ represents $-CF_3$ or $ORf^b$ wherein $Rf^b$ represents a perfluoroalkyl group having 1-5 carbon atoms.

Examples of the non-perfluoro fluorine rubber include a vinylidene fluoride (VdF) fluorine rubber, tetrafluoroethylene (TFE)/propylene (Pr) fluorine rubber, tetrafluoroethylene (TFE)/propylene (Pr)/vinylidene fluoride (VdF) fluorine rubber, ethylene (Et)/hexafluoropropylene (HFP) fluorine rubber, ethylene (Et)/hexafluoropropylene (HFP)/vinylidene fluoride (VdF) fluorine rubber, ethylene (Et)/hexafluoropropylene (HFP)/tetrafluoroethylene (TFE) fluorine rubber, fluorosilicone fluorine rubber and fluorophosphazene fluorine rubber. They can be used alone or in combinations. In addition, these fluorine rubbers may be a copolymer with co-monomer.

The co-monomer is not particularly limited as long as it can copolymerize with other monomer, and include, for example, TFE, HFP, PAVE, chlorotrifluoroethylene (CTFE), trifluoroethylene, trifluoropropylene, tetrafluoropropylene, pentafluoropropylene, trifluorobutene, tetrafluoroisobutene, hexafluoroisobutene, vinyl fluoride, an iodine-containing and fluorine-containing vinyl ether, perfluorovinyl ether such as a fluorine-containing monomer of the formula (b):

$$CH_2=CFRf^b \quad (b)$$

wherein $Rf^b$ is a straight or branched fluoroalkyl group having 1-12 carbon atoms;
a fluorine-containing monomer (c);

$$CF_2=CFOCF_2ORf^c \quad (c)$$

wherein $Rf^c$ is a straight or branched perfluoroalkyl group having 1-6 carbon atoms, a cyclic perfluoroalkyl group having 5-6 carbon atoms or a straight or branched perfluorooxyalkyl group having 1-3 oxygen atoms and 2-6 carbon atoms;
a fluorine-free monomer such as ethylene (Et), propylene (Pr), alkyl vinyl ether; and, a reactive emulsifier. They can be used alone or in combination with two or more.

Examples of the copolymer include, but are not particularly limited to, for example, at least one copolymer selected from the group consisting of a VdF/HFP copolymer, a VdF/TFE/HFP copolymer, a VdF/CTFE copolymer, a VdF/CTFE/TFE copolymer, a VdF/PAVE copolymer, a VdF/TFE/PAVE copolymer, a VdF/HFP/PAVE copolymer, a VdF/HFP/TFE/PAVE copolymer, a VdF/TFE/propylene(Pr) copolymer, a VdF/ethylene(Et)/HFP copolymer and a copolymer of VdF/the fluorine-containing monomer (b) of the formula (b).

The reactive site with a nitrileoxide group in the fluorine rubber may be derived from a monomer having the reactive site or may be introduced by modifying a fluorine rubber having no reactive site.

Examples of the monomer having a reactive site with a nitrileoxide group include, for example, a bisolefin compound of the formula:

$$R^{22}R^{23}C=CR^{24}-Z-CR^{25}=CR^{26}R^{27}$$

wherein $R^{22}$, $R^{23}$, $R^{24}$, $R^{25}$, $R^{26}$ and $R^{27}$ are same or difference, and are independently represent a hydrogen atom or an alkyl group having 1-5 carbon atoms; and Z represents a straight or branched alkylene or an cycloalkylene group having 1-18 carbon atoms which may have an oxygen atom and preferably fluorinated at least partially, or a (per)fluoropolyoxyalkylene group.

Other examples of the monomer having a reactive site with a nitrileoxide group include an olefin compound having a nitrile group, for example, a compound of the formula:

$$R^{28}R^{29}C=CR^{30}-Z-CN$$

wherein $R^{28}$, $R^{29}$ and $R^{30}$ are same or different, and independently represent a hydrogen atom or an alkyl group having 1-5 carbon atoms; and Z represents a straight or branched alkylene or an cycloalkylene group having 1-18 carbon atoms which may have an oxygen atom and preferably fluorinated at least partially or a (per)fluoropolyoxyalkylene group, representatively, $CF_2=CFOCF_2CF(CF_3)OCF_2CF_2CN$.

In one embodiment, the composition of the present invention is used as a raw material of a liquid rubber.

The composition of the present invention used as the raw material of a liquid rubber (hereinafter, referred to as "Liquid rubber raw composition 1") contains at least one present compound (I).

By mixing Liquid rubber raw composition 1 with a composition containing a compound having an unsaturated bond (hereinafter, "Liquid rubber raw composition 2"), a click-reaction between the nitrileoxide group contained in the compound of the present invention and the unsaturated bond contained in the compound in Liquid rubber raw composition 2 occurs to produce a gel-like production (that is, a liquid rubber).

Examples of the compound having an unsaturated bond in contained in Liquid rubber raw composition 2 include, but are not limited to, one or more compounds of the formula:

$$CH_2=CH-(X)_a-Rf^2-(X)_a-CH=CH_2$$

wherein:
X is each independently $-CH_2-$, $-CH_2O-$, $-CH_2OCH_2-$, or $-CH_2-NR^1-CO-$;
Y is $-CH_2-$;
$Rf^1$ is a di-valent perfluoroalkylene group; and
a is each independently an integer of 0 or 1;
and
one or more compounds of the formula:

$$Rf^2-(X)_a-CH=CH_2$$

wherein:
X is each independently $-CH_2-$, $-CH_2O-$, $-CH_2OCH_2-$ or $-CH_2-NR^1-CO-$;
Y is $-CH_2-$;
$Rf^2$ is a perfluoropolyalkyl group; and
a is each independently an integer of 0 or 1.

Specific examples of the compound having an unsaturated bond contained in Liquid rubber raw composition include, for example, triallyl isocyanurate (TAIC), triallyl trimellitate, diallyl phthalate, triallyl phosphite, N,N-diallyl acrylamide, 1,6-vinyl dodecafluorohexane, bismaleimide, triallyl phosphate, and the like.

In the conventional producing of a liquid rubber, a metal catalyst such as a platinum compound was essential. However, the present invention has an advantage to be able to produce a liquid rubber simply by mixing Liquid rubber raw composition 1 and Liquid rubber raw composition 2. By using the composition of the present invention, a catalyst-free liquid rubber can be produced. For example, such liquid rubber can be suitably used in the semiconductor manufacturing process on which the presence of the metal can adversely affect.

In the conventional producing of a liquid rubber, a curing reaction is performed by hydrosililation, and a liquid rubber obtained by this method contains Si atom. This backbone containing Si atom has low resistance against a fluorine active species (a fluorine gas, a fluorine plasma, a fluorine radical) and is not suitable for use in a step in which the active species is generated in the semiconductor manufacturing process. Since the liquid rubber obtained by using the composition of the present invention is produced without using a backbone containing Si atom, the liquid rubber containing no Si atom can be easily produced if necessary. In this point, the present invention is advantageous.

In addition, the present invention provides a liquid rubber produced by using the composition of the present invention.

Hereinbefore, the present invention is described in detail, although the present is not limited to these compounds and uses.

EXAMPLES

Example 1

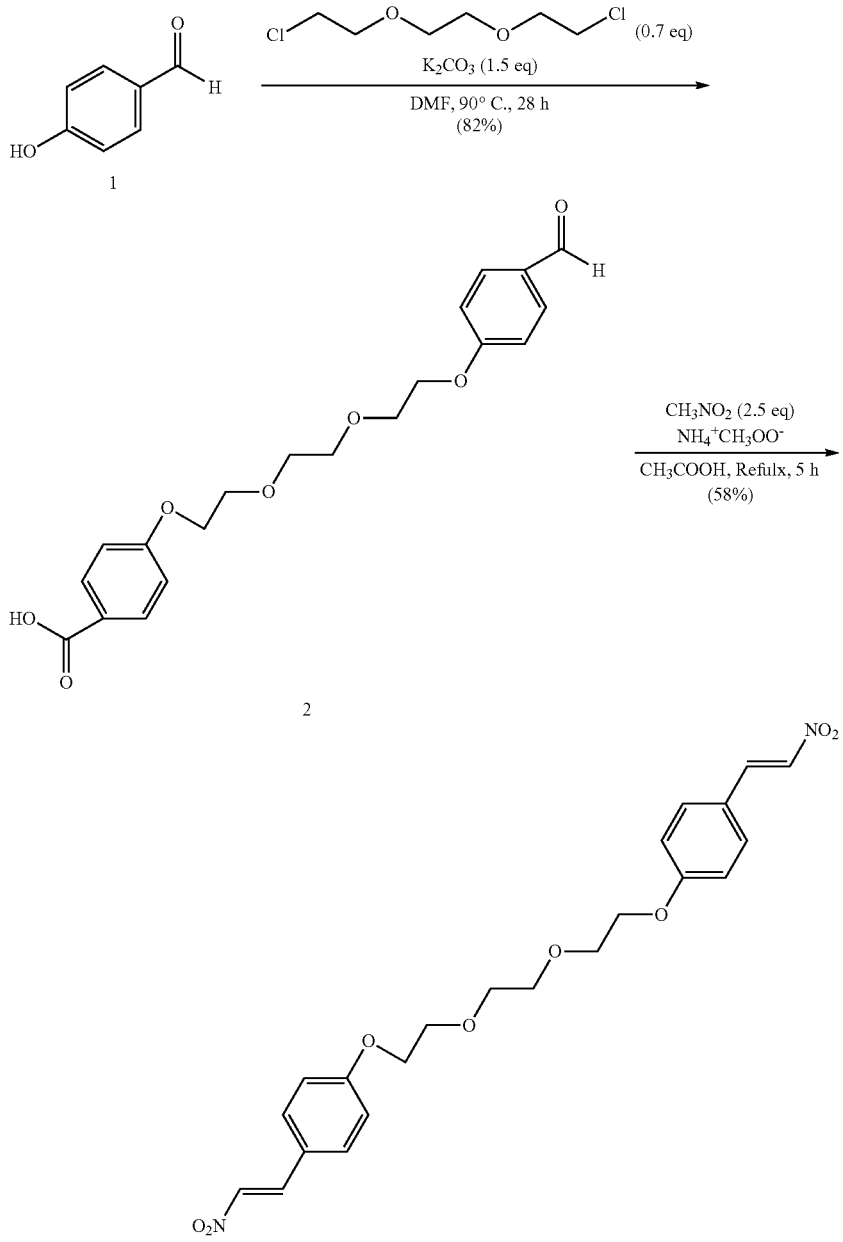

Step 1: Synthesis of difunctional benzaldehyde 2

4-hydroxybenzaldehyde 1 (18 g, 150 mmol), 1,2-bis-(2-chloroethoxyl)ethane (9.4 g, 50 mmol) and potassium carbonate (31 g, 230 mmol) were added to dimethylformamide (250 mL), and reacted at 90° C. for 28 h. Dichloromethane (200 mL) was added, and the mixture was extracted with water 2 times, followed by aqueous sodium hydrogen carbonate solution. Magnesium sulfate was added to the mixture to dry the mixture. The mixture was concentrated with an evaporator, and purified by a silica gel column chromatography (ethyl acetate:hexane=1:1) to obtain the title compound as a white powder (15 g, 41 mmol, 82%).

$^1$H NMR (400 MHz, 298 K, CDCl$_3$): δ 9.88 (s, 2H), 7.82-7.81 (d, J=8.8 Hz, 4H), 7.02-7.00 (d, J=8.8 Hz, 4H), 4.21-4.20 (t, J=4.4 Hz 4H), 3.91-3.88 (t, J=4.4 Hz, 4H) 3.76 (s, 4H) ppm Step 2: Synthesis of difunctional nitroethene 3

Difunctional benzaldehyde 2 (5.4 g, 15 mmol) obtained in Step 1, nitromethane (4.6 g, 75 mmol) and ammonium acetate (1.5 g, 23 mmol) were added to acetic acid (15 mL), and refluxed at 130° C. for 5 hours. Dichloromethane (200 mL) was added, and the mixture was extracted with water 3 times, followed by aqueous sodium hydrogen carbonate solution 1 time. Magnesium sulfate was added to the mixture to dry the mixture. The mixture was concentrated with an evaporator, and purified by a silica gel column chromatography (ethyl acetate:hexane=1:1) to obtain the title compound as a yellow powder (3.9 g, 8.7 mmol, 58%).

$^1$H NMR (400 MHz, 298 K, CDCl$_3$): δ 7.98-7.94 (d, J=9.0 Hz, 2H), 7.55-7.52 (d, J=9.0 Hz, 2H), 7.49-7.47 (d, J=8.8 Hz, 4H), 7.02-7.00 (d, J=8.8 Hz, 4H), 4.21-4.20 (t, J=4.4 Hz 4H), 3.91-3.88 (t, J=4.4 Hz, 4H) 3.76 (s, 4H) ppm Step 3: Synthesis of difunctional t-Bu nitrileoxide 4

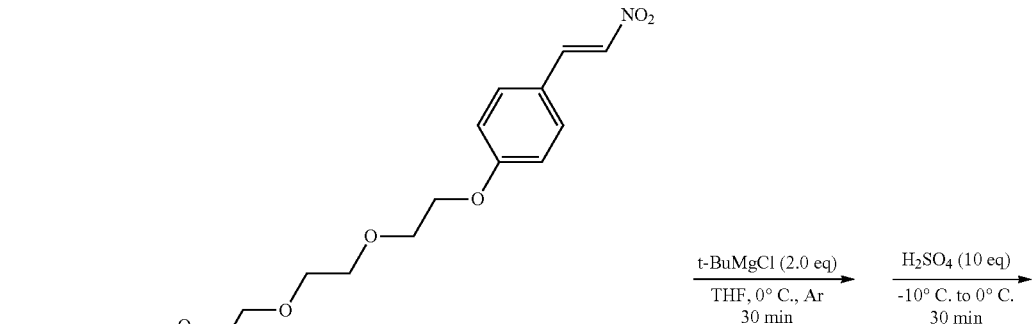

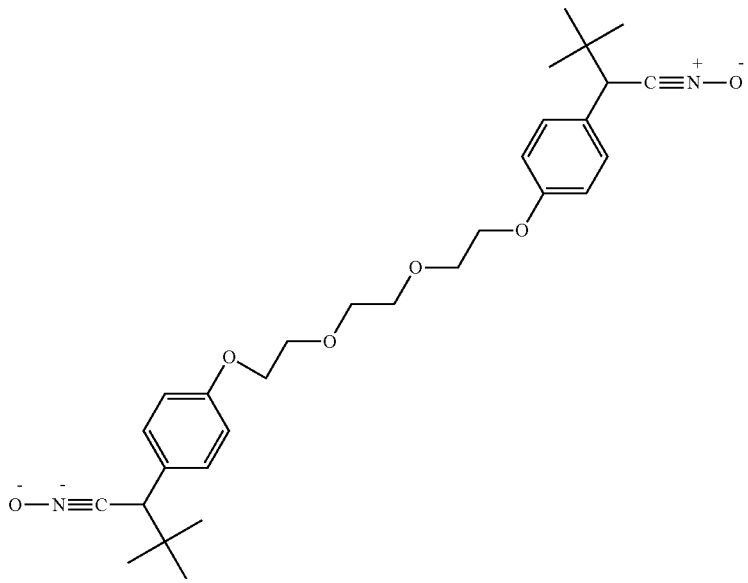

Figure 2:
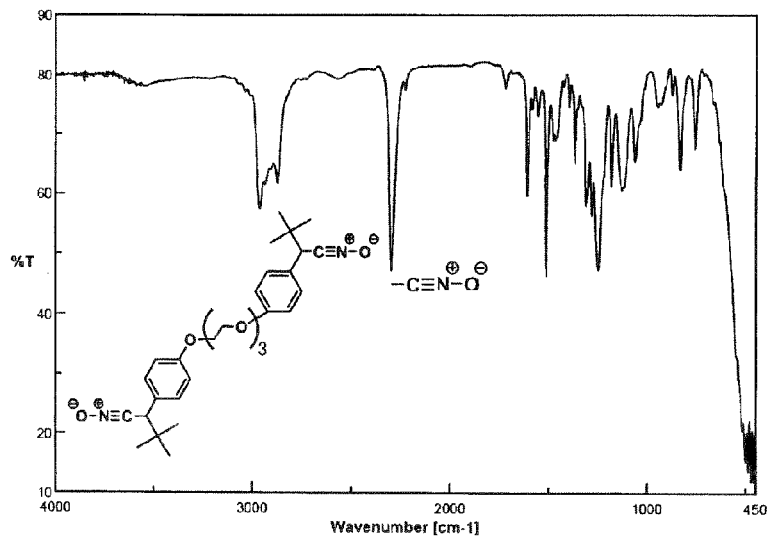
FIG. 2 shows IR spectrum for difunctional t-butyl nitrileoxide 4 in Example 1.

Difunctional nitrostyrene 3 (2.4 g, 5.4 mmol) was added to tetrahydrofuran (250 mL), and cooled to 0° C. under an Ar atmosphere. Tert-butyl magnesium chloride (6.5 mL, 13 mmol) was added, and the mixture was stirred at 30 minutes. After cooling the mixture to −10° C., concentrated sulfuric acid (>95%, 5.7 mL, 100 mmol) was added, and the mixture was stirred for 30 minutes. The mixture was extracted with water 3 times and dried over magnesium sulfate. The solvent was distilled off under reduced pressure, and the mixture was purified by silica gel column chromatography (dichloromethane:hexane=3:1) to obtain the title compound as a yellow oil (1.2 g, 2.3 mmol, 43%). $^1$H-NMR spectrum and IR spectrum are shown in FIG. 1 and FIG. 2, respectively.

$^1$H NMR (400 MHz, 298 K, CDCl$_3$): δ 7.11-7.13 (d, J=8.7 Hz, 4H), 6.87-6.89 (d, J=8.7 Hz, 4H), 4.13-4.12 (t, J=4.0 Hz 4H), 3.88-3.87 (t, J=4.0 Hz, 4H), 3.76 (s, 4H), 3.68 (s, 2H), 1.00 (s, 18H) ppm IR (NaCl): n 2961, 2294, 1609, 1512, 1367, 1309, 1248, 1181, 1127, 1062, 832, 756, 487, 471, 457 cm$^{-1}$ FAB-HR MS (m/z): calculated for C$_{30}$H$_{40}$N$_2$O$_6$Na$^+$: [M+Na]$^+$547.2784. found: 547.2781.

Example 2

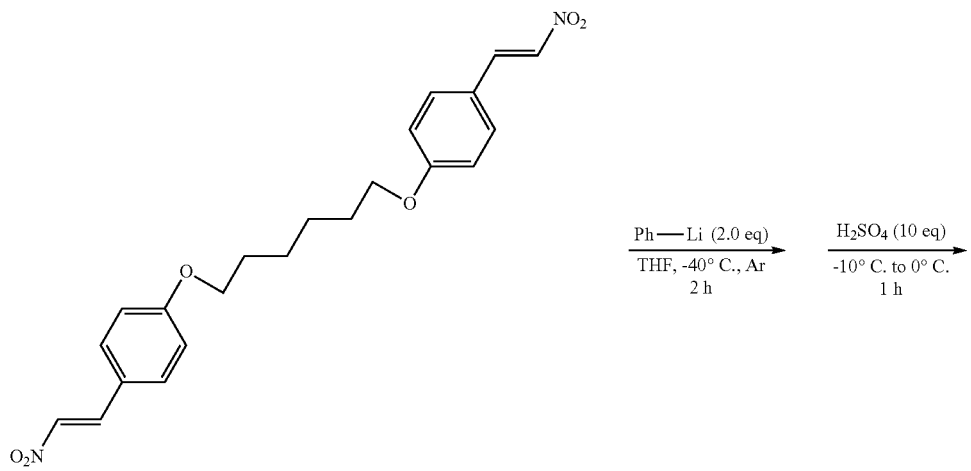

5

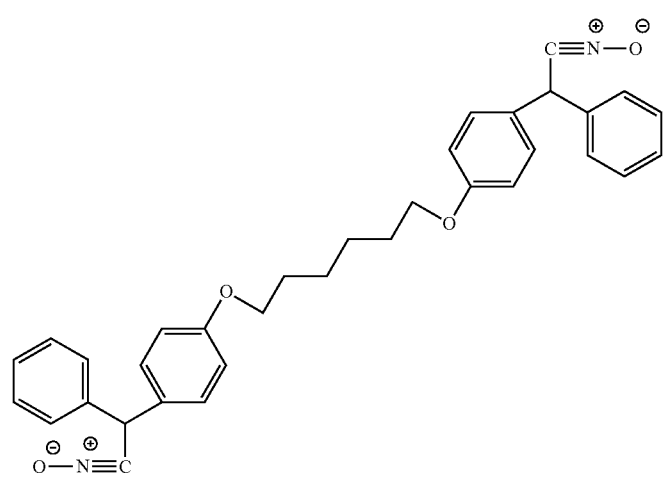

6

Synthesis of difunctional phenyl nitrileoxide 6

Difunctional nitroethene 5 (0.44 g, 1.1 mmol) was added to anhydrous tetrahydrofuran (10 mL) and cooled to −40° C. under an Ar atmosphere. Phenyl lithium (2.4 mL, 4.3 mmol) was slowly added, and the mixture was stirred for 2 hours. After cooling the mixture to −10° C., concentrated sulfuric acid (>95%, 1.0 mL, 20 mmol) was added, and the mixture was stirred at 0° C. for 1 hour. The mixture was extracted with water 3 times and dried over magnesium sulfate. The solvent was distilled off under reduced pressure to obtain the title compound as a pale yellow oil.

Example 3

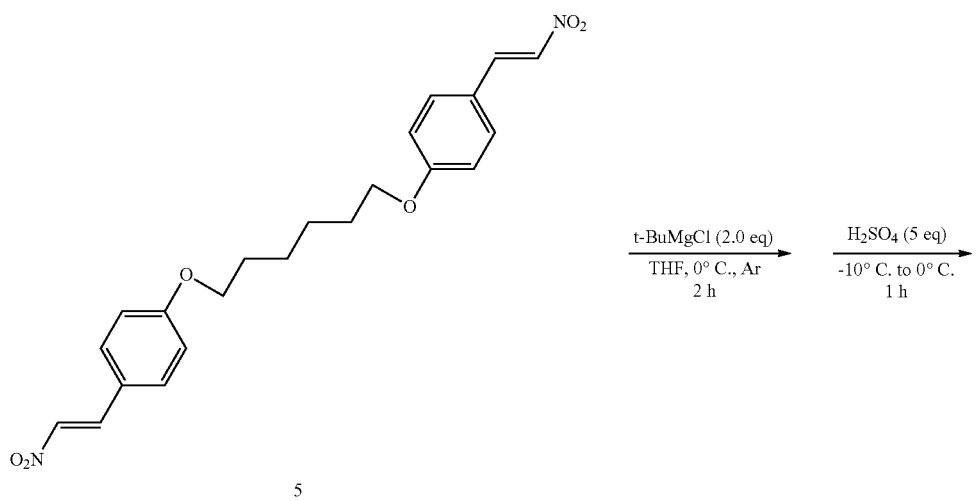

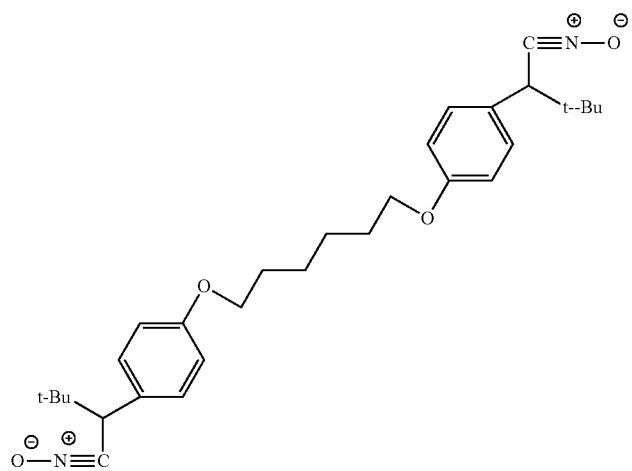

Synthesis of difunctional t-butyl nitrileoxide 7

Difunctional nitroethene 5 (0.21 g, 0.50 mmol) was added to anhydrous tetrahydrofuran (5 mL), and cooled to 0° C. under an Ar atmosphere. Tert-butyl magnesium chloride (1.0 mL, 2.0 mmol) was added, and the mixture was stirred for 1 hour. After cooling the mixture to −10° C., concentrated sulfuric acid (>95%, 1.1 mL, 22 mmol) was added, and the mixture was stirred at 0° C. for 1 hour. The mixture was extracted with water 3 times and dried over magnesium sulfate. The solvent was distilled off under reduced pressure to obtain the title compound as a brown crystal.

Example 4

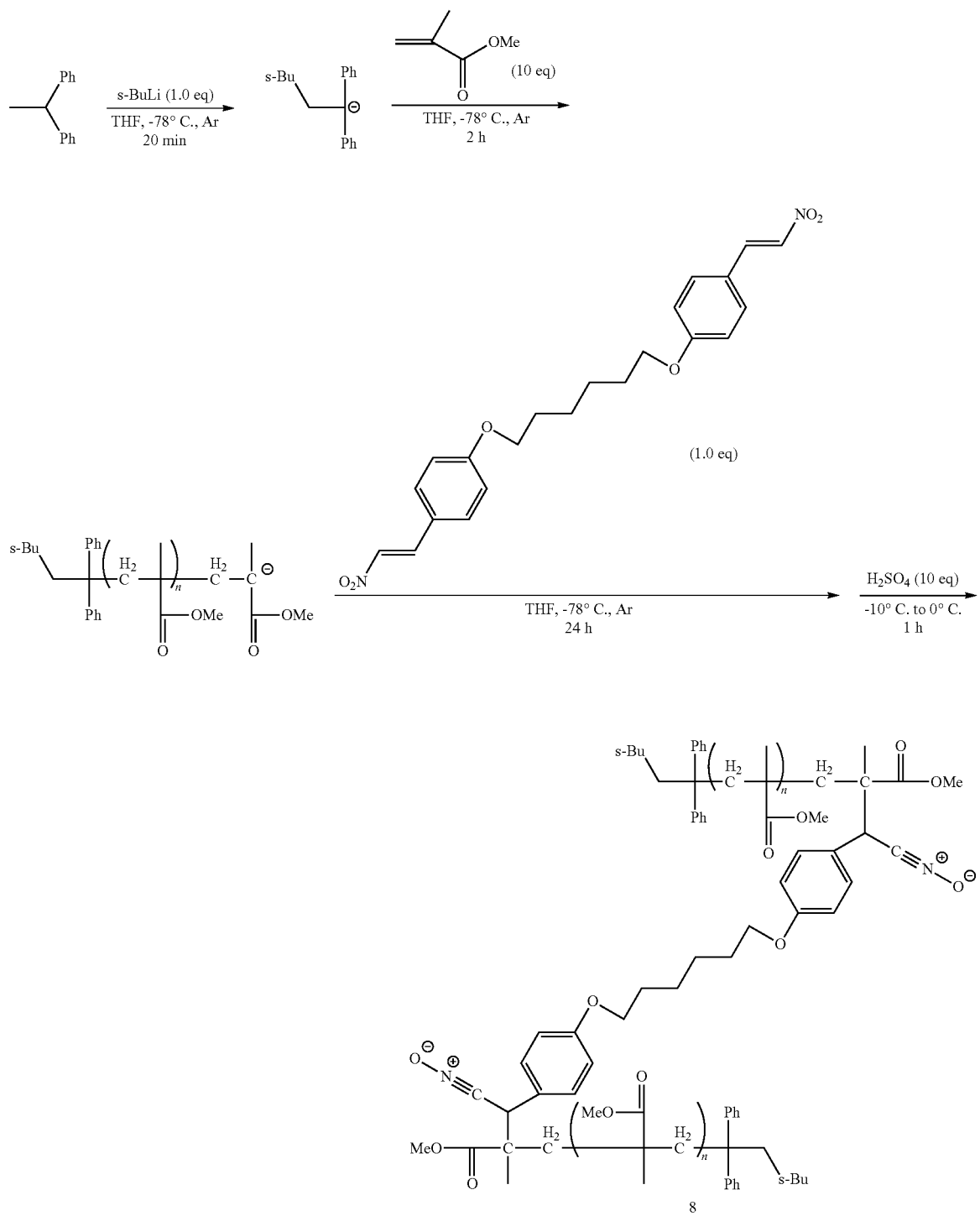

Synthesis of difunctional polymethyl methacrylate nitrileoxide 8

1,1-diphenylethene (1.4 g, 7.9 mmol) was added anhydrous tetrahydrofuran (100 mL) and cooled to −78° C. under an Ar atmosphere. sec-butyl lithium (7.8 mL, 8.2 mmol) was added, and stirred for 20 minutes. Methyl methacrylate (8.5 mL, 80 mmol) was added, and the mixture was stirred for 2 hours to obtain polymethyl methacrylate anion solution. Difunctional nitrostyrene (1.6 g, 4.0 mmol) was added to anhydrous tetrahydrofuran (200 mL) and cooled to −78° C. under an Ar atmosphere. Polymethyl methacrylate anion solution (100 mL) was added, and the mixture was stirred for 24 hours. After cooling the mixture to −10° C., concentrated sulfuric acid (>95%, 4.3 mL, 80 mmol) was added, and the mixture was stirred at 0° C. for 1 hour. The mixture was extracted with water 3 times and dried over magnesium sulfate. The solvent was distilled off under reduced pressure and reprecipitation with methanol was performed to obtain the title compound as a yellow crystal.

Example 5

Cross-linking reaction of difunctional t-butyl nitrileoxide 4 synthesized in Example 1 (hereinafter, simply referred to as "Nitrileoxide 7") and a polymer

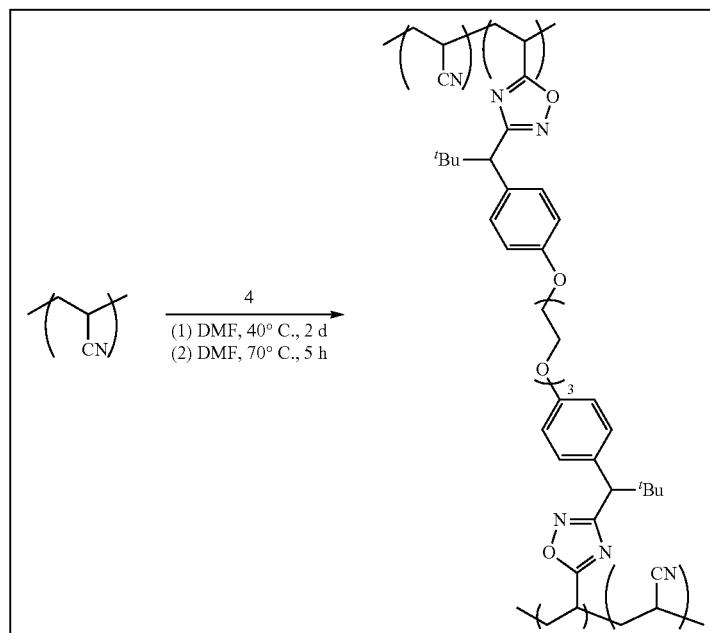

(1) Cross-Linking of polyacrylonitrile (PAN) in N,N-dimethylformamide (DMF)

PAN (0.054 g) was dissolved in DMF (1 mL) at a room temperature, and Nitrileoxide 4 (0.01 g) was added and reacted at 40° C. for 2 days. After the reaction, the mixture was repeatedly washed with DMF and dried to obtain a pale yellow network polymer (0.050 g, 78%). Chloroform-Swelling ratio by weight of this network polymer was 2,100%.

(2) Cross-Linking of PAN in DMF

PAN (0.054 g) was dissolved in DMF (1 mL) at a room temperature, and Nitrileoxide 4 (0.01 g) was added and reacted at 70° C. for 5 hours. After the reaction, the mixture was repeatedly washed with DMF and dried to obtain a Pale yellow network polymer (0.061 g, 95%). Chloroform-Swelling ratio by weight of this network polymer was 2,100%.

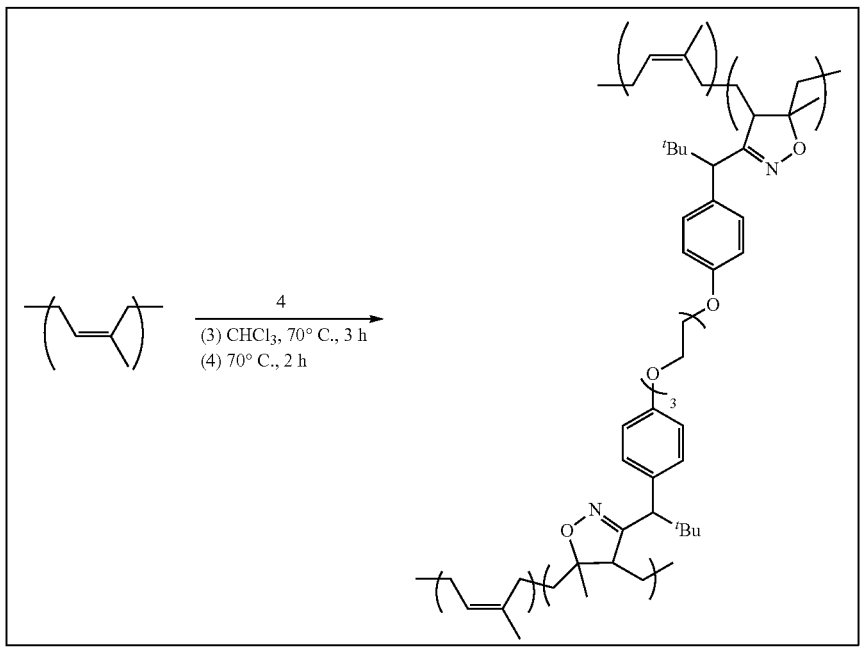

(3) Cross-Linking of a Natural Rubber (NR) in Chloroform

NR (0.069 g) was dissolved in chloroform (1 mL) at a room temperature, and Nitrileoxide 4 (0.011 g) was added and reacted at 70° C. for 3 hours. After the reaction, the mixture was repeatedly washed with chloroform and dried to obtain a colorless network polymer (0.057 g, 72%). Chloroform-Swelling ratio by weight of this network polymer was 2,700%.

(4) Cross-Linking of NR in a Solid Phase

NR (0.068 g) and Nitrileoxide 4 (0.010 g) were mixed on the mortar at 70° C. for 2 hours. After the reaction, the mixture was repeatedly washed with chloroform and dried to obtain a colorless network polymer (0.048 g, 61%). Chloroform-Swelling ratio by weight of this network polymer was 2,100%.

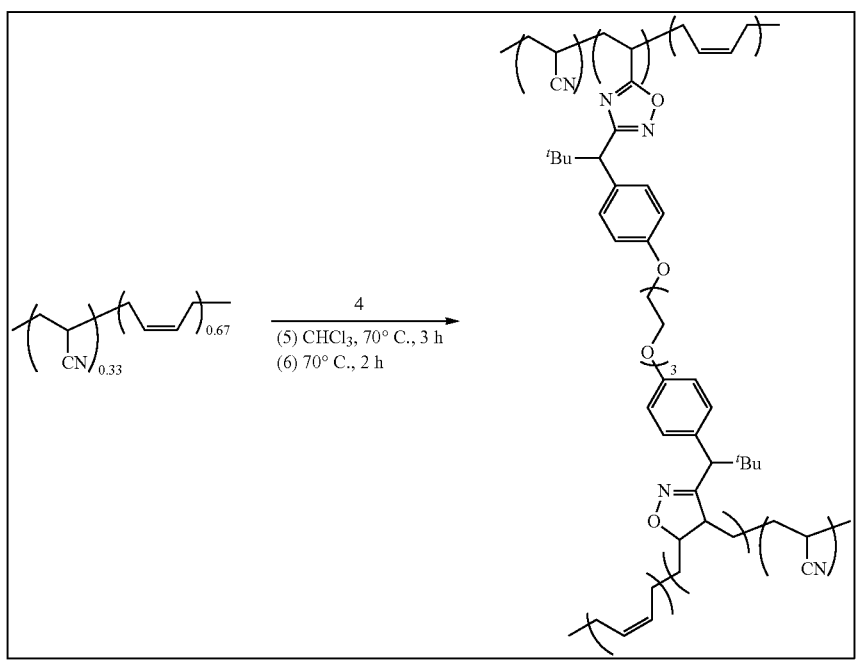

(5) Cross-Linking of an Acrylonitrile-Butadiene Rubber (NBR) in Chloroform

NBR (0.055 g) was dissolved in chloroform (1 mL) at a room temperature, and Nitrileoxide 4 (0.011 g) was added and reacted at 70° C. for 2 hours. After the reaction, the mixture was repeatedly washed with chloroform and dried to obtain a colorless network polymer (0.042 g, 64%). Chloroform-Swelling ratio by weight of this network polymer was 2,200%.

(6) Cross-Linking of NBR in a Solid Phase

NBR (0.054 g) and Nitrileoxide 4 (0.010 g) were stirred on the mortar at 70° C. for 2 hours. After the reaction, the mixture was repeatedly washed with chloroform and dried to obtain a colorless network polymer (0.046 g, 71%). Chloroform-Swelling ratio by weight of this network polymer was 3,100%.

The results in the above (1) to (6) are shown in the following table.

TABLE 1

| Polymer | Solvent | Temperature (° C.) | Time (hour) | Yield | Swelling ratio (%) |
|---|---|---|---|---|---|
| (1) PAN | DMF | 40 | 48 | 78 | 2100 |
| (2) PAN | DMF | 70 | 5 | 95 | 2100 |
| (3) NR | chloroform | 70 | 3 | 72 | 2700 |
| (4) NR | — | 70 | 2 | 61 | 2100 |
| (5) NBR | chloroform | 70 | 2 | 64 | 2200 |
| (6) NBR | — | 70 | 2 | 71 | 3100 |

From the above results, it is confirmed that the compound of the present invention is reacted with various polymers (PAN, NR, NBR). In addition, as shown in (4) and (6), it is confirmed that even when no solvent is used, the reaction proceeds very well. Furthermore, all polymers of a raw material could be dissolved in chloroform, the network polymers obtained after the reaction could not be dissolved and showed 2,100 to 3,100% of chloroform-swelling ratio by weight. Therefore, it is confirmed that the polymers are cross-linked by the nitrileoxide.

Example 6

Formation of a Film by Cross-Linking of a Neutral Rubber (NR)

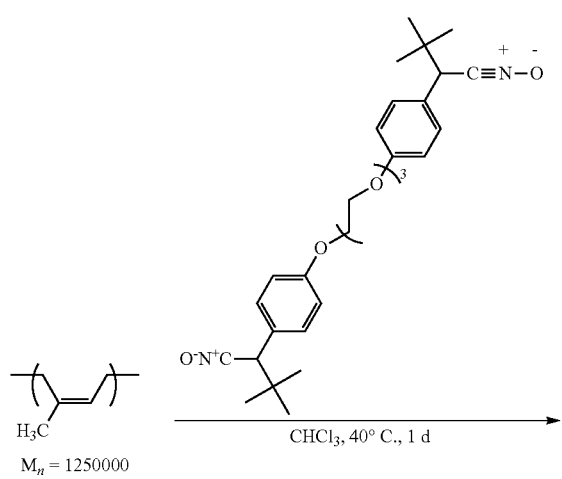

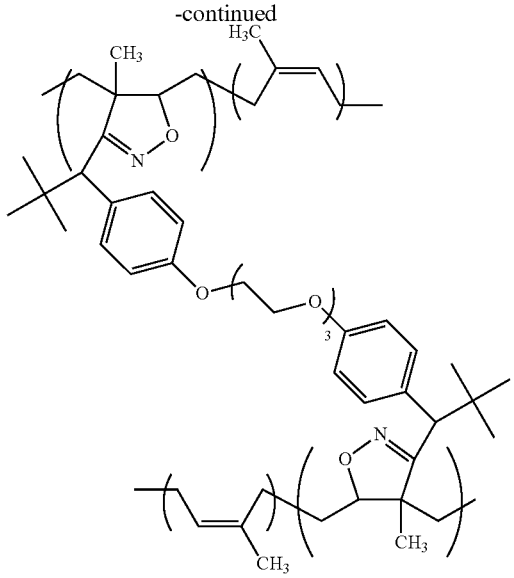

(1): Natural rubber (1.0 g) was dissolved in chloroform (15 mL) in Teflon petri dish (42 mmϕ), and a solution in which Nitrileoxide 4 (100 mg; 0.20 mmol) was dissolved in chloroform (% mL) was added and stirred. After removing the stirrer, the reaction was progressed on a hot plate at 40° C. under air for 1 day. The film produced was washed with chloroform, and then dried at a room temperature under air and at 70° C. under vacuum to obtain a pale yellow network polymer film (1) (1.0 g; 91%).

(2) to (4): Network polymer films (2) to (4) were obtained similarly to the above (1) except that the amount of Nitrileoxide 4 was changed to (2) 85 mg (0.17 mmol), (3) 50 mg (0.10 mmol) and (4) 20 mg (0.04 mmol).

For Network polymer films (1) to (4), acrylonitril-swelling ratio by weight was measured. In addition, concentration of the cross-linking chain per volume (network chain concentration (cross-linking density): ν) was calculated by using modified Flory-Reighner equality:

$$\nu = -\frac{g}{V}\left[\frac{\ln(1-V_R) + V_R + \mu V_R^2}{g^{2/3}V_R^{1/3} - V_R/2}\right]$$

wherein

ν is a network chain concentration (mol/cm$^3$),

V is a molecular volume of swelling solvent (molecular weight/density) (cm$^3$/mol), g is a volume fraction of gel-rubber in a sample piece before swelling, μ is a interaction constant between a sample rubber and a swelling solvent, $V_R$ is a volume fraction of rubber in the swollen gel-rubber.

Furthermore, a proportion of reacted double bonds in a polymer (degree of cross-linking) was calculated. The results are shown in the following table. It is noted that the degree of cross-linking was calculated by the following equality.

$$\text{(Degree of cross-linking)} = \text{(number of cross-linked double bonds)}/$$
$$\text{(total number of double bonds of charged natural rubber)} =$$
$$\text{(the number of cross-linked chain)} \times$$
$$2/\text{(the total number of double bonds of used natural rubber)} =$$
$$v \times \text{(gel volume)} \times 2/\text{(the total number of double bonds of}$$
$$\text{used natural rubber)} = v \times \text{(total weight of the gel)}/$$
$$\text{(gel density)} \times 2/[\text{(used natural rubber weight)}/$$
$$\text{(repeat molecular weight of natural rubber)}]$$

TABLE 2

| | Amount added of nitrileoxide (wt % (mol %)) | Swelling ratio by weight (%) | Cross-linking density (mol/cm$^3$) | Degree of cross-linking (%) | Yield (%) |
|---|---|---|---|---|---|
| (1) | 10 (1.3) | 900 | 1.6 × 10$^4$ | 2.5 | 91 |
| (2) | 8.5 (1.1) | 1000 | 1.3 × 10$^4$ | 2.1 | 90 |
| (3) | 5.0 (0.65) | 1800 | 5.4 × 10$^5$ | 0.86 | 93 |
| (4) | 2.0 (0.26) | 2700 | 2.7 × 10$^5$ | 0.41 | 83 |

Figure 3:
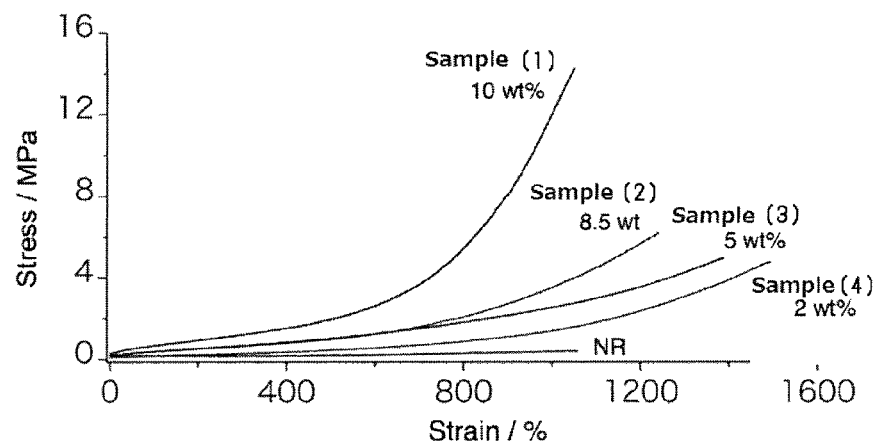
FIG. 3 shows the results of the tension test in Example 6.

For Network polymer films (1) to (4) (Width: 2 mm, length: 12 mm, thickness: 250 μm), a tension test was performed to obtain a stress-strain curve. The results are shown in FIG. 3 together with the result of a natural rubber which had not been reacted the nitrileoxide as a control.

From the above results, it is confirmed that the network polymer film obtained by reacting Nitrileoxide 4 with NR was cross-linked. From the above results, it is confirmed that the cross-linking density and the degree of cross-inking increases with increasing the amount used of Nitrileoxide 4, and Nitrileoxide 4 is quantitatively reacted. This can be confirmed from the fact that the strength against the strain increases with increasing the amount used in the tension test.

Example 7

Difunctional nitrileoxide 6 synthesized in Example 2 (199 mg, white-yellow solid) and triallyl isocyanurate (264 mg, colorless liquid) were adequately mixed to obtain a pasty liquid. This pasty liquid was added on a cell for viscoelasticity measurement, and the cell was set in a viscoelasticity measuring apparatus. Then, the temperature inside of the cell was raised from a room temperature to 120° C. and this temperature was maintained. For 30 minutes, a change of viscosity was observed, as a result, the increase in the viscosity was observed. In addition, a progress of the curing reaction was confirmed from the fact that there was a yellow transparent solid (gel) substance in the cell after the measurement. It is noted that as the viscoelasticity measuring apparatus, Rheosol-G3000NT (manufactured by UBM Co., Ltd.) was used.

COMPARATIVE EXAMPLE

Triallyl isocyanurate (500 mg, colorless liquid) was added on a cell for viscoelasticity measurement, and the cell was set in a viscoelasticity measuring apparatus. Then, the temperature inside of the cell was raised from a room temperature to 120° C. and this temperature was maintained. For 30 minutes, a change of viscosity was observed, as a result, the increase in the viscosity was not observed. In the cell after the measurement, there was only colorless liquid whose appearance did not change from the measurement, therefore it was confirmed that the curing reaction did not proceed. It is noted that as the viscoelasticity measuring apparatus, the above apparatus was used.

Example 8

Synthesis of Trifunctional Aliphatic Nitrileoxide

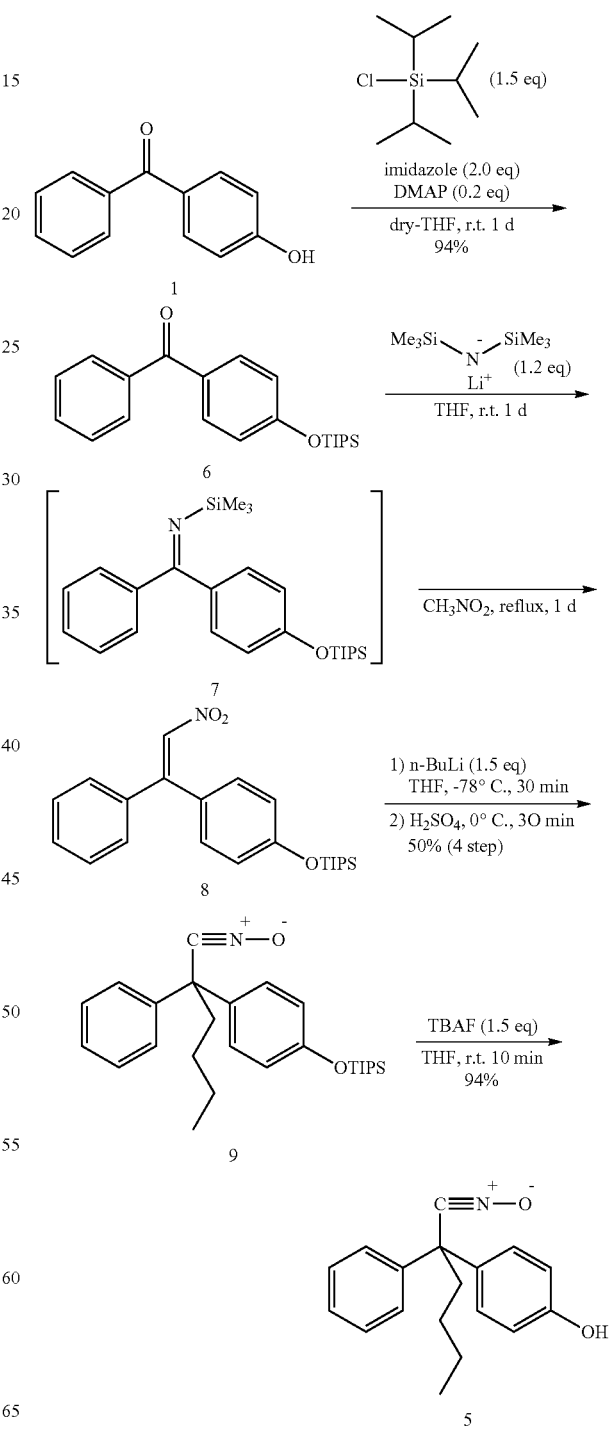

Step 1: Synthesis of triisopropylsilyl (TIPS) benzophenone 6 p-OH benzophenone (15 g, 75 mmol), imidazole (10 g, 150 mmol), DMAP (1.8 g, 15 mmol) were dissolved in anhydrous THF (150 mL), and triisopropylsilyl chloride (22 g, 110 mmol) was added at 0° C. The temperature was returned to a room temperature and the mixture was reacted for 1 day. The solvent was distilled off under reduced pressure, and an appropriate amount of dichloromethane was added. The mixture was washed with water 3 times, and dried over magnesium sulfate. The solvent was distilled off under reduced pressure and the mixture was purified by silica gel column chromatography (ethyl acetate:hexane=1:1) to obtain a pale yellow oil (25 g, 71 mmol, 94%).

7.78-7.75 (d, J=8.1 Hz, 2H), 7.78-7.76 (d, J=8.8 Hz, 4H), 7.56-7.54 (t, J=8.8 Hz, 1H), 7.49-7.45 (t, 8.8 Hz, 2H), 6.95-6.92 (d, J=8.8 Hz, 2H), 1.59-1.28 (m, 3H), 1.12-1.11 (d, J=7.3 Hz, 18H) ppm

Step 2: Synthesis of TIPS diphenyl nitroethene 8

TIPS benzophenone 6 (7.3 g, 21 mmol) was added to THF (20 mL) and cooled to 0° C. under an Ar atmosphere. Lithium bis(trimethyisilyl)amide (19 mL, 25 mmol) was added, and the mixture was stirred at a room temperature for 1 day. The solvent was distilled off under reduced pressure, and an appropriate amount of ethyl acetate was added. The mixture was washed with water 2 times and brine 1 time. The solvent was distilled off under reduced pressure, nitromethane (50 mL) was added thereto, and the mixture was refluxed at 115° C. for 1 day. The solvent was distilled off to obtain a brown oil. This compound itself was used in a next reaction.

Step 3: Synthesis of TIPS diphenyl nitrileoxide 9

The oil obtained in Step 2 (7.0 g) was added to anhydrous THF (200 mL), and cooled to −78° C. under an Ar atmosphere. n-BuLi (10 mL, 26 mmol) was added, and the mixture was stirred for 30 minutes. Concentrated sulfuric acid (>95%, 9.5 mL, 175 mmol) was added, and the mixture was stirred at 0° C. for 30 minutes. The mixture was washed with water 4 times and dried over magnesium sulfate. The solvent was distilled off under reduced pressure, and the mixture was purified by a silica gel column chromatography (dichloromethane:hexane=1:2) to obtain a yellow oil (4.6 g, 11 mmol, 50%).

$^1$H NMR (400 MHz, 298 K, CDCl$_3$): δ 7.34-7.25 (m, J=8.7 Hz, 5H), 7.13-7.11 (d, J=8.7 Hz, 2H), 6.83-6.81 (d, J=8.7 Hz, 2H), 2.34-2.30 (t, J=7.1 Hz, 2H), 1.34-1.22 (m, 7H), 1.12-1.09 (d, J=7.3 Hz, 18H), 0.89-0.86 (t, J=7.1 Hz, 3H) ppm

Step 4: Synthesis of OH diphenyl nitrileoxide 5

Figure 4:
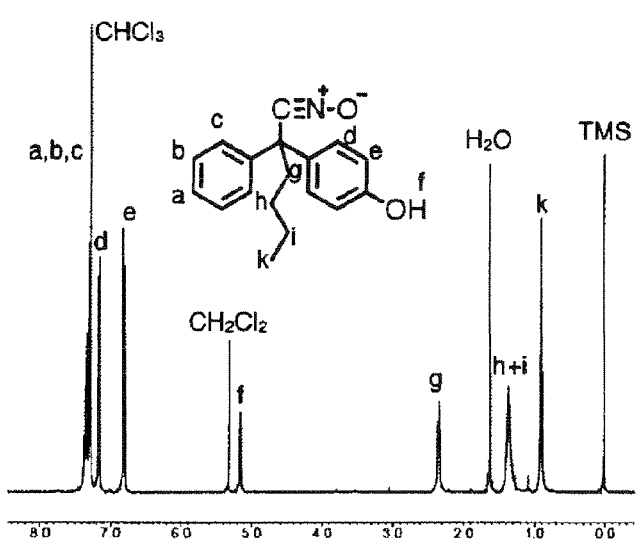
FIG. 4 shows ¹H-NMR spectrum for OH-diphenyl-nitrileoxide 5 in Example 8.
Figure 5:
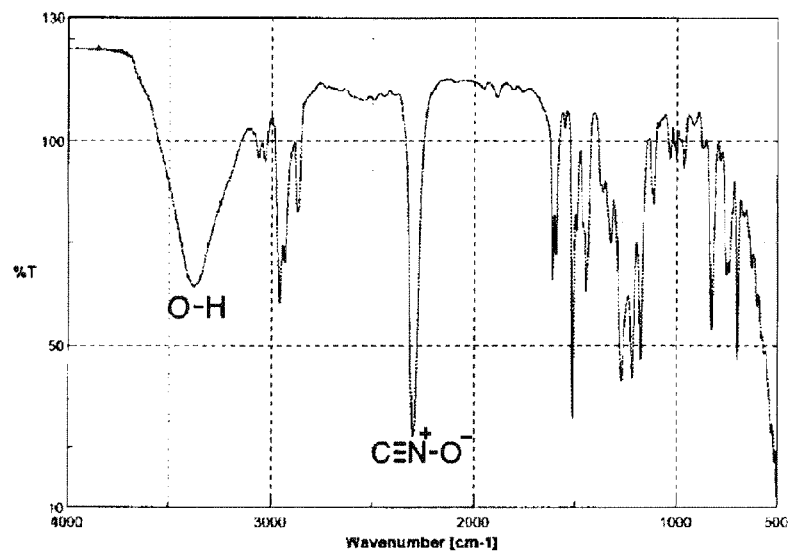
FIG. 5 shows IR spectrum for OH-diphenyl-nitrileoxide 5 in Example 8.

TIPS diphenyl nitrileoxide 9 (2.0 g, 4.5 mmol) was dissolved in THF (50 mL), and tetrabutylammonium fluoride (TBAF) (1.7 mL, 6.7 mmol) was added and stirred for 10 minutes. An appropriate amount of dichloromethane was added, and the mixture was washed with water 3 times and brine 1 time and dried over magnesium sulfate. The solvent was distilled off under reduced pressure, and the mixture was purified by a silica gel column chromatography (dichloromethane:hexane=6:1) to obtain a yellow oil (1.2 g, 4.2 mmol, 94%). $^1$H-NMR spectrum and IR spectrum are shown in FIG. 4 and FIG. 5, respectively.

$^1$H NMR (400 MHz, 298 K, CDCl$_3$): δ 7.37-7.28 (m, J=8.7 Hz, 5H), 7.18-7.16 (d, J=8.7 Hz, 2H), 6.82-6.80 (d, J=8.7 Hz, 2H), 5.16 (s, 1H), 2.38-2.34 (t, J=6.8 Hz, 2H), 1.37 (m, 4H), 0.93-0.89 (t, J=6.8 Hz, 3H) ppm

Step 5: Synthesis of trifunctional nitrileoxide 11

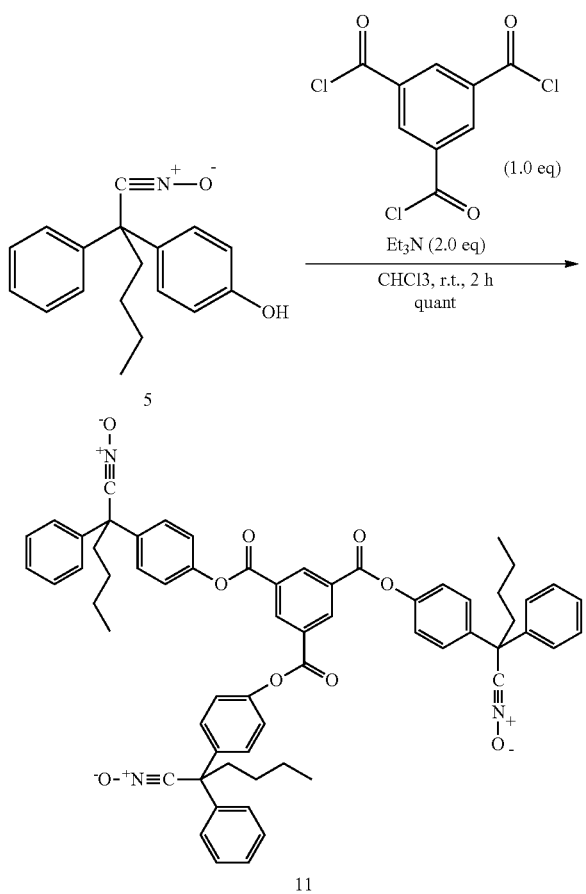

Figure 6:
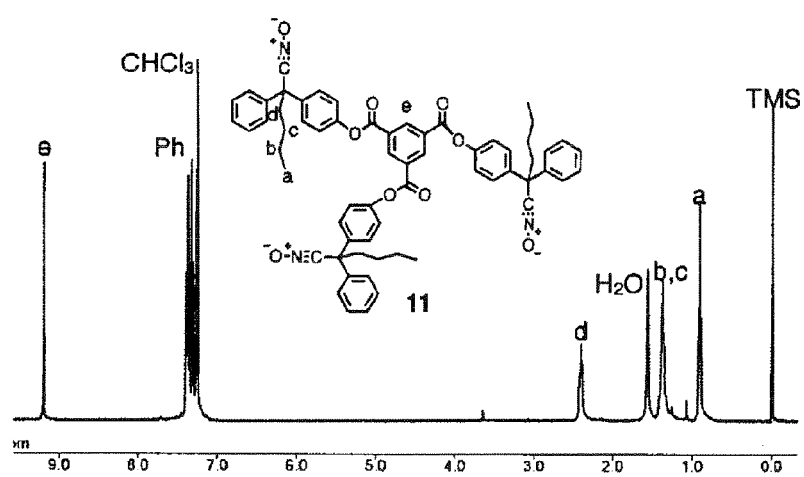
FIG. 6 shows ¹H-NMR spectrum for trifunctional nitrileoxide 11 in Example 8.
Figure 7:
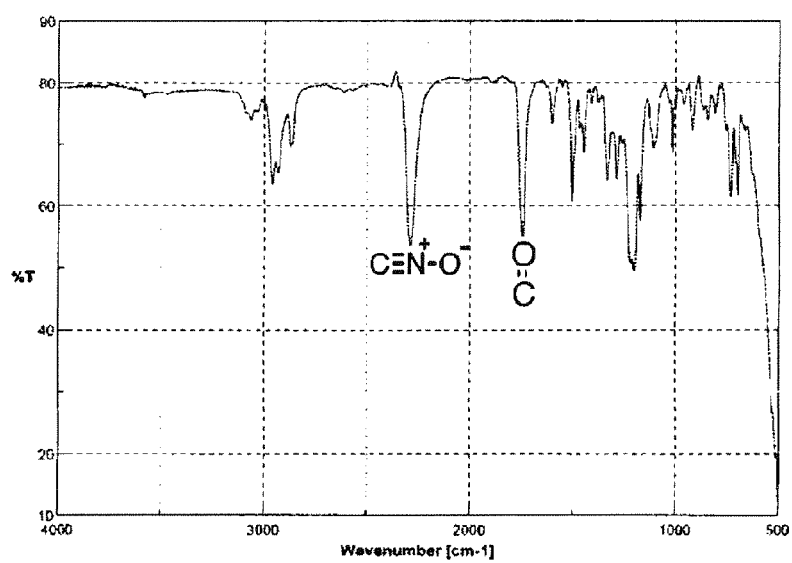
FIG. 7 shows IR spectrum for trifunctional nitrileoxide 11 in Example 8.

OH diphenyl nitrileoxide 5 (0.43 g, 1.5 mmol) was dissolved in chloroform (10 mL), and triethylamine (0.43 mL, 3.1 mmol) was added. The solution was cooled to 0° C., and a solution in which trimesoyl chloride (0.12 g, 0.45 mmol) was dissolved in chloroform (5 mL) was added. The temperature was returned to a room temperature, and the mixture was stirred for 2 hours. The mixture was washed with water 2 times and brine 1 time, and dried over magnesium sulfate. The solvent was distilled off under reduced pressure to obtain a pale yellow solid (0.43 g, 4.3 mmol, 96%). $^1$H-NMR spectrum and IR spectrum are shown in FIG. 6 and FIG. 7, respectively.

$^1$H NMR (400 MHz, 298 K, CDCl$_3$): δ 9.20 (s, 3H), 7.40-7.25 (m, 27H), 2.40 (t, J=6.9 Hz, 6H), 1.38 (m, 12H), 0.90-0.89 (t, J=6.9 Hz, 9H) ppm

INDUSTRIAL APPLICABILITY

The compound of the present invention can be suitably used in various applications, for example, as a surface treatment agent, a filler modifier, a fiber treatment agent, a compatibilizing agent, a cross-linking agent or a modifier of adhesive, or as a raw a liquid rubber.

The invention claimed is:

1. A compound of the formula (I):

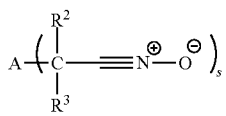

wherein:
R² and R³ represent each independently a hydrogen atom or a hydrocarbon group;
A represents an s-valent organic group; and
s is an integer of 2-10.

2. The compound as claimed in claim 1 wherein s is 2 or 3.

3. The compound as claimed in claim 1 which is represented by the formula (II):

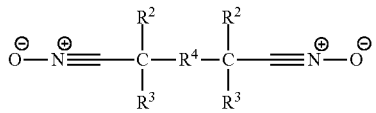

wherein:
R² and R³ represent each independently a hydrogen atom or a hydrocarbon group; and
R⁴ represents a di-valent hydrocarbon group;
provided that each of R², R³ and R⁴ binds to a carbon atom to which a nitrileoxide is attached at a carbon atom thereof.

4. The compound as claimed in claim 1 wherein R² and R³ are each independently a hydrogen atom, or an alkyl group, a cycloalkyl group, a heterocycloalkyl group, an aryl group, a heteroaryl group or a (poly)alkylether group which may have one or more substituents.

5. The compound as claimed in claim 1 wherein at least one of R² and R³ is an aryl group, a tert-alkyl group, a sec-alkyl group or a (poly)alkylether group which may be substituted by one or more substituents.

6. The compound as claimed in claim 3 wherein R⁴ is a group of the formula:

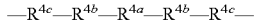

wherein:
R⁴ᵃ represents an alkylene group or a di-valent (poly)alkylether group which may have one or more substituents;
R⁴ᵇ represents each independently a bond, an oxygen atom, or an alkylene group which may have one or more substituents; and
R⁴ᶜ represents each independently a bond, or an alkylene group, a cycloalkylene group or an arylene group which may have one or more substituents.

7. The compound as claimed in claim 6 wherein R⁴ᵇ is —OCO— or —COO—.

8. The compound as claimed in claim 3 wherein R⁴ is a group of the formula:

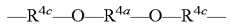

wherein:
R⁴ᵃ represents an alkylene group or a di-valent (poly)alkylether group which may be substituted by one or more substituents; and
R⁴ᶜ represents an arylene group.

9. The compound as claimed in claim 1 which is represented by the formula (III):

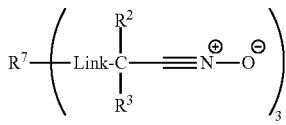

wherein:
R⁷ represents a tri-valent organic group;
R² and R³ represent each independently a hydrogen atom or a hydrocarbon group; and
Link represents a bond or a di-valent group;
provided that each of R², R³ and Link binds to a carbon atom to which a nitrileoxide is attached at a carbon atom thereof.

10. The compound as claimed in claim 9 wherein Link represents —R⁴ᵃ—, —R⁴ᵇ— or —R⁴ᶜ—, or a group in which two or more of —R⁴ᵃ—, —R⁴ᵇ— and —R⁴ᶜ— are linked:
wherein R⁴ᵃ represents an alkylene group or a di-valent (poly)alkylether group which may have one or more substituents;
R⁴ᵇ represents each independently a bond, an oxygen atom, or an alkylene group which may have one or more substituents; and
R⁴ᶜ represents each independently a bond, or an alkylene group, a cycloalkylene group or an arylene group which may have one or more substituents.

11. The compound as claimed in claim 9 wherein the Link is an oxygen atom, a sulfur atom, an alkylene group, an alkyleneoxy group, an alkylenedioxy group, a carbonyl group, —O—CO—, —CO—O—, —O—CO—O—, —NR—, —C(O)NR—, —NR—CO—NR— (wherein R is a hydrogen atom or an alkyl group or an aryl group which may have one or more substituents), an arylene group, an aryleneoxy group, an arylenedioxy group, or a group in which two or more of them are linked.

12. The compound as claimed in claim 9 wherein R⁷ is C(R) (R is a hydrogen atom or an alkyl group which may be substituted by a fluorine atom), a nitrogen atom, an optionally substituted silicon atom, or a tri-valent aromatic ring which may have a heteroatom as a ring member atom.

13. A composition comprising one or more compounds as claimed in claim 1.

14. A composition for applying to a material containing a group reactive with a nitrileoxide group, which comprises one or more compounds as claimed in claim 1.

15. The composition as claimed in claim 13 which is a cross-linking agent.

16. The composition as claimed in claim 13 which is a raw material of for a liquid rubber.

17. A composite of two or more compounds which are treated with the cross-linking agent as claimed in claim 15.

18. A liquid rubber produced by using the composition as claimed in claim 16.

* * * * *